(12) United States Patent
Djebara et al.

(10) Patent No.: US 9,620,293 B2
(45) Date of Patent: Apr. 11, 2017

(54) HERMETICALLY SEALED CAPACITOR FOR AN IMPLANTABLE MEDICAL DEVICE

(71) Applicant: AVX Corporation, Fountain Inn, SC (US)

(72) Inventors: Lotfi Djebara, Paris (FR); Radek Matousek, Trebova (CZ); Ludek Kubes, Lanskroun (CZ)

(73) Assignee: AVX Corporation, Fountain Inn, SC (US)

( * ) Notice: Subject to any disclaimer, the term of this patent is extended or adjusted under 35 U.S.C. 154(b) by 103 days.

(21) Appl. No.: 14/542,761

(22) Filed: Nov. 17, 2014

(65) Prior Publication Data

US 2016/0141110 A1  May 19, 2016

(51) Int. Cl.
| | |
|---|---|
| H01G 9/145 | (2006.01) |
| H01G 9/10 | (2006.01) |
| A61N 1/39 | (2006.01) |
| H01G 9/00 | (2006.01) |
| H01G 9/02 | (2006.01) |
| H01G 9/042 | (2006.01) |
| H01G 9/048 | (2006.01) |
| H01G 9/07 | (2006.01) |

(52) U.S. Cl.
CPC .......... *H01G 9/10* (2013.01); *A61N 1/3956* (2013.01); *H01G 9/0029* (2013.01); *H01G 9/02* (2013.01); *H01G 9/042* (2013.01); *H01G 9/048* (2013.01); *H01G 9/07* (2013.01); *H01G 9/145* (2013.01)

(58) Field of Classification Search
CPC .......... H01G 9/145; H01G 9/10; H01G 9/025; H01G 9/028
See application file for complete search history.

(56) References Cited

U.S. PATENT DOCUMENTS

| | | |
|---|---|---|
| 5,104,738 A | 4/1992 | Brow et al. |
| 5,111,327 A | 5/1992 | Blohm et al. |
| 5,369,547 A | 11/1994 | Evans |
| 5,457,862 A | 10/1995 | Sakata et al. |
| 5,473,503 A | 12/1995 | Sakata et al. |
| 5,648,302 A | 7/1997 | Brow et al. |
| 5,729,428 A | 3/1998 | Sakata et al. |
| 5,812,367 A | 9/1998 | Kudoh et al. |
| 6,197,252 B1 | 3/2001 | Bishop et al. |
| 6,322,912 B1 | 11/2001 | Fife |
| 6,391,275 B1 | 5/2002 | Fife |
| 6,416,730 B1 | 7/2002 | Fife |

(Continued)

*Primary Examiner* — Nguyen Ha
(74) *Attorney, Agent, or Firm* — Dority & Manning, P.A.

(57) ABSTRACT

A wet electrolytic capacitor is provided that includes an anode, an anode lead, an electrolyte, a casing having a wall that defines an anode lead orifice, and a sealing assembly. The sealing assembly is connected to the casing at the anode lead orifice, and a portion of the anode lead extends through it. The sealing assembly includes an isolation tube, a metal plate, and an elastomeric ring. The tube receives the anode lead and has a first portion extending through the anode lead orifice and a second portion located in an interior of the casing. The plate is positioned adjacent to an exterior surface of the wall, covers the anode lead orifice, and contains an orifice through which the first portion of the tube extends. The ring is positioned adjacent to an interior surface of the wall and contains an orifice through which the second portion of the tube extends.

24 Claims, 9 Drawing Sheets

(56) References Cited

U.S. PATENT DOCUMENTS

| | | | |
|---|---|---|---|
| 6,517,892 B1 * | 2/2003 | Sakai | H01G 9/0036 29/25.03 |
| 6,527,937 B2 | 3/2003 | Fife | |
| 6,576,099 B2 | 6/2003 | Kimmel et al. | |
| 6,592,740 B2 | 7/2003 | Fife | |
| 6,594,140 B1 | 7/2003 | Evans et al. | |
| 6,635,729 B1 | 10/2003 | Groenendaal et al. | |
| 6,639,787 B2 | 10/2003 | Kimmel et al. | |
| 6,952,339 B1 * | 10/2005 | Knowles | H01G 9/042 29/25.03 |
| 6,987,663 B2 | 1/2006 | Merker et al. | |
| 7,206,186 B1 | 4/2007 | Knight et al. | |
| 7,220,397 B2 | 5/2007 | Kimmel et al. | |
| 7,341,705 B2 | 3/2008 | Schnitter | |
| 7,365,960 B2 | 4/2008 | O'Phelan et al. | |
| 7,381,396 B2 | 6/2008 | Thomas et al. | |
| 7,419,926 B2 | 9/2008 | Schnitter et al. | |
| 7,483,260 B2 | 1/2009 | Ziarniak et al. | |
| 7,515,396 B2 | 4/2009 | Biler | |
| 8,279,585 B2 | 10/2012 | Dreissig et al. | |
| 8,300,387 B1 * | 10/2012 | Zednickova | H01G 9/08 361/518 |
| 8,780,530 B2 * | 7/2014 | Zednicek | H01G 9/10 361/516 |

* cited by examiner

HERMETICALLY SEALED CAPACITOR FOR AN IMPLANTABLE MEDICAL DEVICE

BACKGROUND OF THE INVENTION

High voltage electrolytic capacitors are employed as energy storage reservoirs in many applications, including implantable medical devices. These capacitors are required to have a high energy density because it is desirable to minimize the overall size of the implanted device. This is particularly true of an implantable cardioverter defibrillator ("ICD"), also referred to as an implantable defibrillator, because the high voltage capacitors used to deliver the defibrillation pulse can occupy as much as one third of the ICD volume. While progress has been made in minimizing the overall size of the capacitors used in ICDs through the use of tantalum-based planar anodes that have a large internal surface area but a very small thickness so that they can be easily incorporated into ICDs, problems still exist. For instance, the planar anodes are anodized and are then sealed in a casing containing a highly conductive and generally corrosive liquid electrolyte solution, where an anode lead extends from the casing. Unfortunately, such wet capacitors can experience problems when the electrolyte leaks from the casing at the seal around the anode lead. For example, gases (e.g., hydrogen) may be evolved during operation, causing pressure to build inside the capacitor.

In light of the above, a gas-tight hermetic seal (e.g., metal-glass-metal hermetic seal) is often employed through which the anode lead can safely extend. However, the metal-glass-metal hermetic seal itself can sometimes become corroded by the liquid electrolyte and leak, and the small thickness of the casing makes designing a metal-glass-metal hermetic seal that can effectively prevent leakage of the electrolyte extremely difficult.

As such, a need currently exists for an improved hermetically sealed wet electrolytic capacitor for use in implantable medical devices, such as defibrillators.

SUMMARY OF THE INVENTION

In accordance with one embodiment of the present invention, a wet electrolytic capacitor for an implantable medical device is disclosed that contains a planar anode, a working electrolyte, a casing, and a sealing assembly. The planar anode includes a porous anode body coated with a dielectric layer, wherein an anode lead extends from the porous anode body, and the working electrolyte is in electrical contact with the planar anode. The planar anode and the working electrolyte are positioned within an interior of the casing, and the casing has a wall that defines an anode lead orifice. The sealing assembly is connected to the casing at the anode lead orifice and includes a metal housing, an elastomeric ring, and a metal plate. The metal housing, which is positioned within the anode lead orifice and extends into the interior of the casing, defines a cavity through which a portion of the anode lead extends. The elastomeric ring, which is positioned within the cavity, contains an orifice through which a portion of the anode lead extends. The metal plate is also positioned within the cavity, and also contains an orifice through which a portion of the anode lead extends. Further, a lower surface of the metal plate is in contact with the elastomeric ring inside the cavity.

In accordance with another embodiment of the present invention, a method for forming a wet electrolytic capacitor for an implantable medical device is disclosed. The method includes positioning a planar porous anode body having an anode lead extending therefrom inside a casing having a sidewall in which an anode lead orifice is formed such that a portion of the anode lead extends through the anode lead orifice, wherein a sealing assembly surrounds the anode lead at the anode lead orifice. The sealing assembly includes a metal housing positioned within the anode lead orifice and extending into an interior of the casing, wherein the metal housing defines a cavity through which a portion of the anode lead extends; an elastomeric ring positioned within the cavity, wherein the elastomeric ring contains an orifice through which a portion of the anode lead extends; and a metal plate positioned within the cavity, wherein the metal plate contains an orifice through which a portion of the anode lead extends, and wherein a lower surface of the metal plate is in contact with the elastomeric ring inside the cavity. The method further includes forming a hermetic seal between the sealing assembly and the anode lead.

Other features and aspects of the present invention are set forth in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
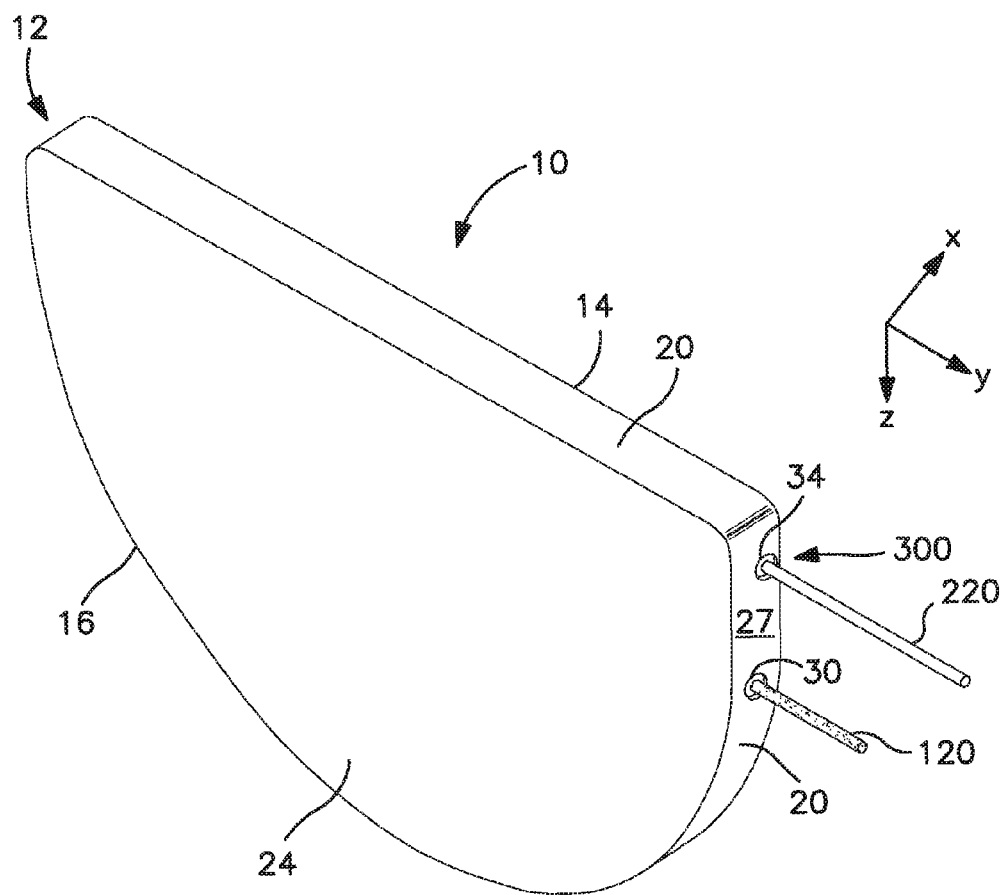
FIG. 1 is a perspective view of one embodiment of the wet electrolytic capacitor of the present invention.

Repeat use of reference characters in the present specification and drawings is intended to represent same or analogous features or elements of the invention.

DETAILED DESCRIPTION OF REPRESENTATIVE EMBODIMENTS

It is to be understood by one of ordinary skill in the art that the present discussion is a description of exemplary embodiments only, and is not intended as limiting the broader aspects of the present invention, which broader aspects are embodied in the exemplary construction.

Generally speaking, the present invention is directed to a wet electrolytic capacitor for an implantable medical device that contains a planar anode including a porous anode body coated with a dielectric layer, an anode lead that extends from the porous anode body, a working electrolyte that is in electrical contact with the planar anode, a casing within which the planar anode and the working electrolyte are positioned and that has a wall that defines an anode lead orifice, and a sealing assembly that is connected to the casing at the anode lead orifice and through which a portion of the anode lead extends. In particular, the sealing assembly includes metal housing, a metal plate, and an elastomeric ring. The metal housing is positioned within the anode lead orifice and extends into an interior of the casing and defines a cavity through which a portion of the anode lead extends. Meanwhile, the elastomeric ring rests inside the cavity, as does the metal plate, where a lower surface of the metal plates is in contact with elastomeric ring inside the cavity. In some embodiments, the elastomeric ring can have a tapered portion that can be positioned inside the cavity, where the cavity is correspondingly tapered to receive the elastomeric ring. The sealing assembly can optionally include an isolation tube receives the anode lead and has a first portion that extends through the anode lead orifice and a second portion that extends through the anode lead orifice into the interior of the casing. Such an arrangement of the sealing assembly creates a hermetic seal at the anode lead orifice. The present invention is also directed to a method for forming a wet electrolytic capacitor for use in an implantable medical device. The method includes positioning a planar porous anode body having an anode lead extending therefrom inside a casing having a sidewall in which an anode lead orifice is formed such that a portion of the anode lead extends through the anode lead orifice, wherein a sealing assembly surrounds the anode lead at the anode lead orifice. The sealing assembly includes a metal housing positioned within the anode lead orifice and extending into an interior of the casing, wherein the metal housing defines a cavity through which a portion of the anode lead extends; an elastomeric ring positioned within the cavity, wherein the elastomeric ring contains an orifice through which a portion of the anode lead extends; and a metal plate positioned within the cavity, wherein the metal plate contains an orifice through which a portion of the anode lead extends, and wherein a lower surface of the metal plate is in contact with the elastomeric ring inside the cavity. The method further includes forming a hermetic seal between the sealing assembly and the anode lead. The present inventors have found that the particular arrangement of the sealing assembly discussed above and including a metal housing, a metal plate, an elastomeric ring, and an optional isolation tube, as well as the method of sealing an anode lead orifice formed in a capacitor casing using the sealing assembly components discussed above, results in a wet electrolytic capacitor having an improved hermetic seal around the anode lead such that the working electrolyte does not leak from the anode lead orifice from which the anode lead extends. For instance, the components in the resulting metal to elastomeric seal can prevent leakage of fluid at the anode lead orifice because the components can be made with very tight tolerances due to the materials utilized. Further, as a result of the small size of the sealing assembly, the thickness of the capacitor casing in which the sealing assembly is utilized can be minimized, which is critical for wet electrolytic capacitors used in ICDs as too thick of a casing makes implantation of the ICDs into the body difficult. On the other hand, glass to metal seals have generally been unsuccessful in preventing such leaks when used in wet electrolytic capacitors. Moreover, without intending to be limited by theory, it is believed that the inclusion of a metal housing in combination with a metal plate can further enhance the effectiveness of the hermetic seal by protecting the elastomeric ring during assembly and by reducing the amount of contact between the elastomeric ring and working electrolyte.

Various embodiments of the present invention will now be described in more detail.

I. Sealing Assembly

Referring to FIGS. 1 and 5-11, one embodiment of a sealing assembly 300 will now be described in more detail. The sealing assembly 300 is connected to the casing 12 of the capacitor 10 and provides a hermetic seal through which the anode lead 220 can safely extend. Specifically, the sealing assembly 300 can hermetically seal an anode lead orifice 34 formed in a sidewall 200 of a casing member 14 of the wet electrolytic capacitor 10 and through which the anode lead 220 of the wet electrolytic capacitor 10 extends (see FIG. 1).

Figure 6:
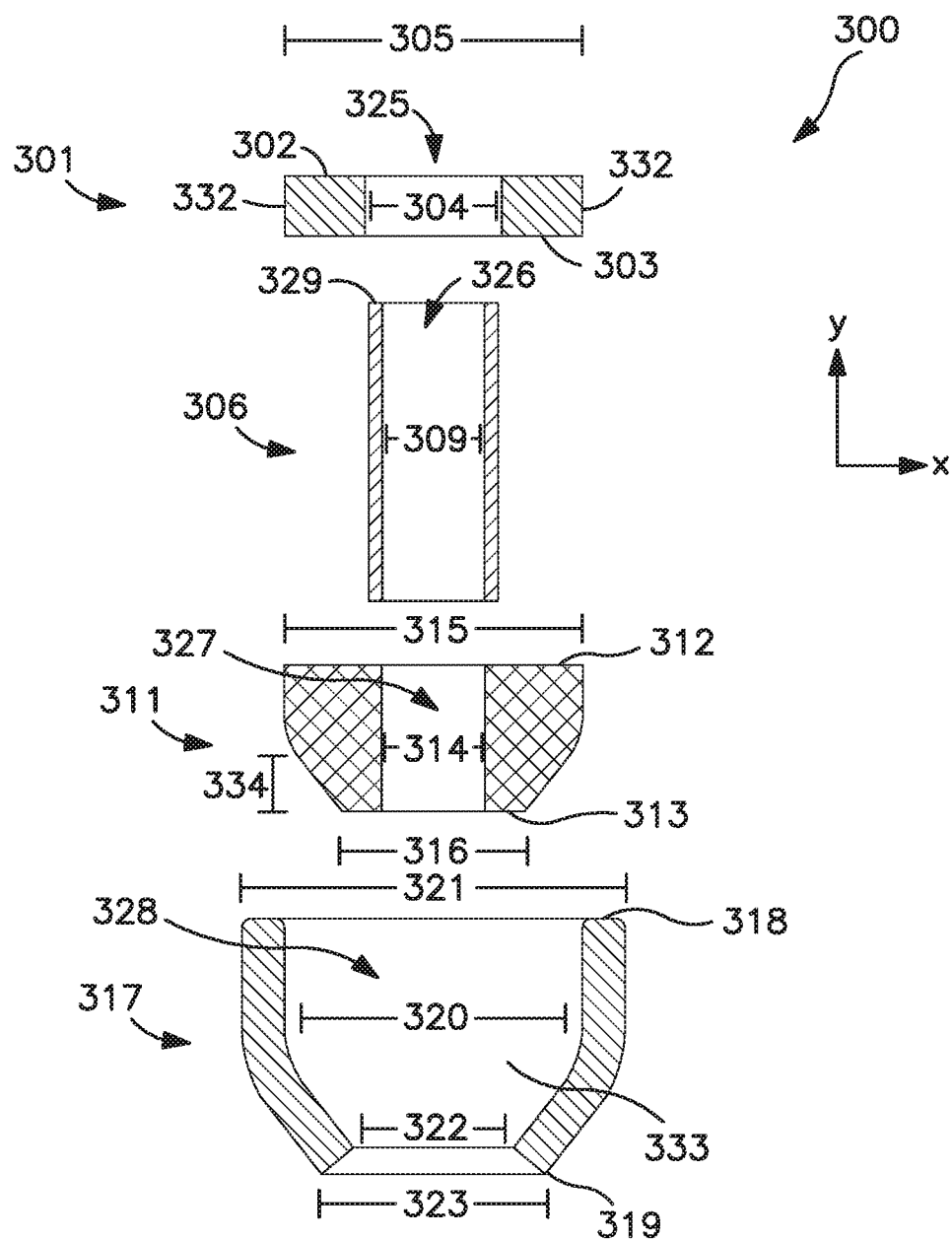
FIG. 6 is an exploded cross-sectional view of the sealing assembly of FIG. 5.
Figure 7:
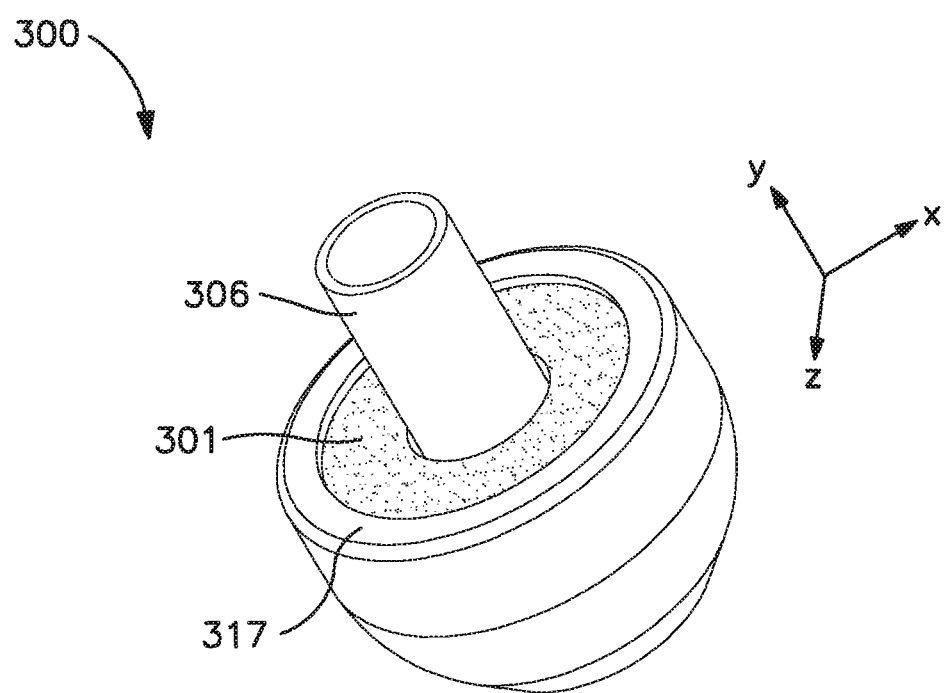
FIG. 7 is an assembled perspective view of the sealing assembly of FIGS. 5 and 6.
Figure 8:
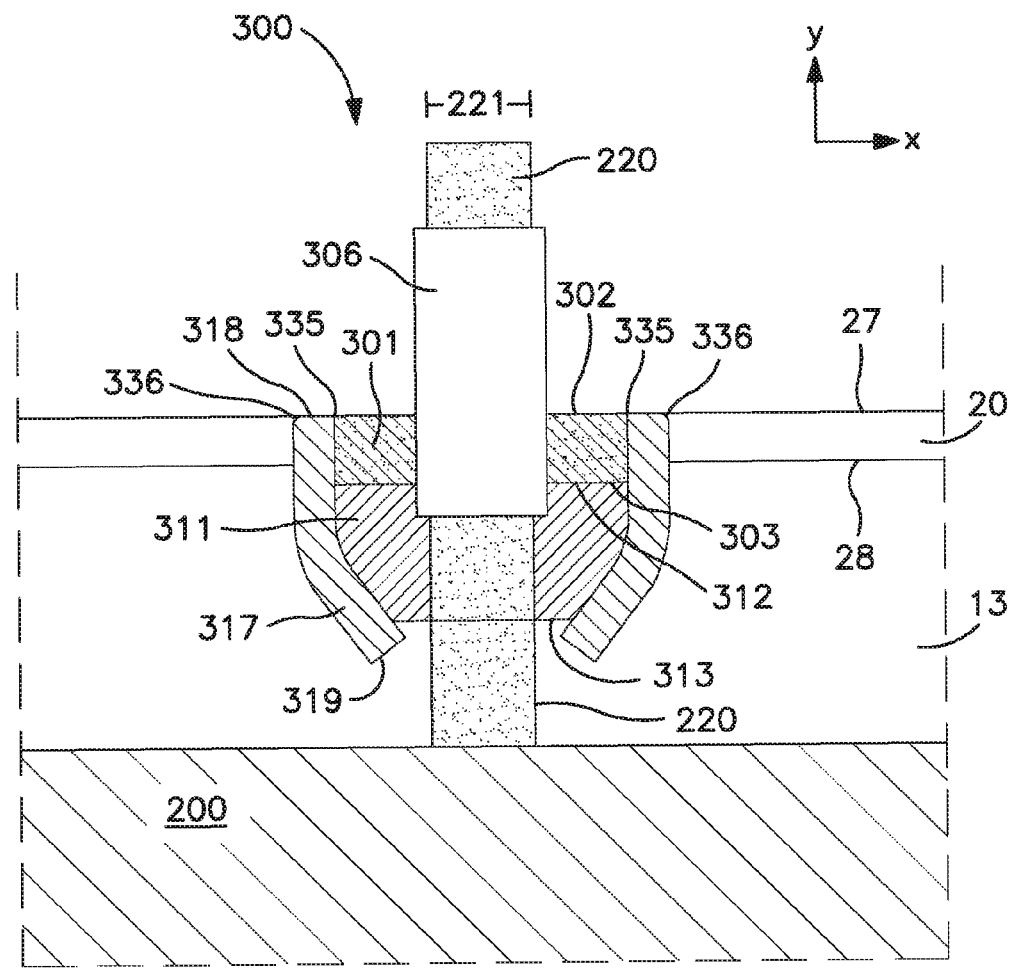
FIG. 8 is a cross-sectional view of a part of the casing after the anode lead has been hermetically sealed using the sealing assembly of FIGS. 5-7.

In one embodiment and as shown in FIGS. 5-11, the sealing assembly 300 includes a metal plate 301, an elastomeric ring 311, and a metal housing 317, where the metal plate 301 and the elastomeric ring 311 include orifices 325 and 327, respectively, that define a channel through which the anode lead 220 an optional isolation tube 306 can extend. Meanwhile, the metal housing 317 includes a cavity 328 in which the elastomeric ring 311 and the metal plate 301 are positioned. Generally, the metal plate 301 is in contact with an upper surface 312 of the elastomeric ring 311 and can serve as a lid to hold the elastomeric ring 311 inside the cavity 328. As shown in FIGS. 6 and 8, the metal plate 301 has an upper surface 302 and a lower surface 303. The metal plate 301 can also have an inner diameter 304 and an outer diameter 305, where the inner diameter 304 defines a metal plate orifice 325 through which the anode lead 220 can extend, where the metal plate 301 is positioned in a cavity 328 of the metal housing 317 at the anode lead orifice 34 formed in the capacitor casing 12. The metal plate orifice 325 as defined by the inner diameter 304 can have a diameter of from about 0.001 millimeters to about 3 millimeters, such as from about 0.005 millimeters to about 2.5 millimeters, such as from about 0.01 millimeters to about 2 millimeters so long as the optional isolation tube 306 and the anode lead 220 that the isolation tube 306 surrounds (if present) can extend through the metal plate orifice 325. Further, the inner diameter 304 of the metal plate 301 can be generally constant throughout the length of the metal plate 301 in the y-direction to maintain snug contact with the anode lead 220 or isolation tube 306 surrounding the anode lead 220, if present. Meanwhile, the outer diameter 305 can be any diameter so long as the metal plate 301 can fit snugly inside the metal housing 317. For instance, the outer diameter can be less than about 8 millimeters, such as from about 0.025 millimeters to about 6.5 millimeters, such as from about 0.05 millimeters to about 5 millimeters, such as from about 0.075 millimeters to about 4 millimeters. In addition, although the metal plate 301 is shown as a circular-shaped ring or disc, this is not required, and the outer dimensions of the metal plate can from any suitable shape, such as an oval, square, rectangle, triangle, etc, so long as the shape matches the shape of the metal housing 317 in which the metal plate 301 is disposed and with which the metal plate 301 creates a snug fit.

Additionally, the elastomeric ring 311 of the sealing assembly 300 has an upper surface 312 and a lower surface 313. The elastomeric ring 311 has an inner diameter 314, a first outer diameter 315 at its upper surface 312, and a second outer diameter 316 at its lower surface 313, where, in some embodiments, the second outer diameter 316 can be smaller than the first outer diameter 315. The inner diameter 314 defines an elastomeric ring orifice 327 through which the optional isolation tube 306 and the anode lead 220 that the isolation tube 306 surrounds (if present) can extend. For example, the elastomeric ring orifice 327 as defined by the inner diameter 314 can have a diameter of from about 0.001 millimeters to about 3 millimeters, such as from about 0.005 millimeters to about 2.5 millimeters, such as from about 0.01 millimeters to about 2 millimeters so long as the anode lead 220 and the optional isolation tube 306 can extend through the elastomeric ring orifice 327 so that the elastomeric ring 311 maintains snug contact with the isolation tube 306 to ensure a tight seal. Further, the inner diameter 314 of the elastomeric ring 311 is generally constant throughout the length of the elastomeric ring 311 in the y-direction to maintain snug contact with the isolation tube 306 surrounding the anode lead 220. Meanwhile, in some embodiments, the upper surface 312 of the elastomeric ring 311 can have a larger first outer diameter 315 which tapers along the length of the elastomeric ring 311 in the y-direction such that the lower surface 313 has a smaller second outer diameter 316. Such tapering can ensure sufficient contact with the metal housing 317 which can support the elastomeric ring 311 and creates a seal with the casing 12 as discussed in more detail below.

Next, the metal housing 317 can have an upper surface 318 and a lower surface 319. The metal housing 317 has first inner diameter 320, a second inner diameter 322, a first outer diameter 321, and a second outer diameter 323. The first inner diameter 320 and second inner diameter 322 define a metal housing cavity 328 through which the anode lead 220 and isolation tube 306, if present, can extend. The first inner diameter 320 of the metal housing 317 can be larger than the second inner diameter 322 such that it can receive and support the metal plate 301 and elastomeric ring 311 while creating a tight or snug fit between the components. Further, the metal housing 317 can be tapered from the upper surface 318 to the lower surface 319 in a similar fashion to the elastomeric ring 311 such that the contact between the elastomeric ring 311 and the metal housing 317 can be increased to ensure a tight seal when the metal plate 301 is placed above the elastomeric ring 311 to serve as a lid to hold the elastomeric ring 311 snugly in place in the metal housing 317. In other words, the upper surface 318 of the metal housing 317 has a larger inner diameter 320 larger and a larger first outer diameter 321 which taper along the length of the metal housing 317 in the y-direction such that the lower surface 319 has a smaller second inner diameter 322 and a smaller second outer diameter 323. For instance, the second inner diameter 322 through which the optional isolation tube 306 and the anode lead 220 can be inserted can have a diameter of from about 0.001 millimeters to about 3 millimeters, such as from about 0.005 millimeters to about 2.5 millimeters, such as from about 0.01 millimeters to about 2 millimeters so long as the isolation tube 306 and the anode lead 220 that it surrounds can extend through the metal housing cavity 328 so that the metal housing 317 maintains snug contact with the anode lead 220 or the isolation tube 306 to ensure a tight seal. Meanwhile, the first inner diameter 320 is large enough to receive the metal plate 301 and the elastomeric ring 311, yet small enough to create a tight seal between the components, such as by laser welding or spot welding. For instance, the first inner diameter 320 can generally have a diameter that is the same as outer diameter 305 of the metal plate 301 and the first outer diameter 315 of the elastomeric ring 311. As such, the metal ring 317 can have a tapered cavity 333 for receiving the elastomeric ring 311 and metal plate 301, as shown specifically in FIGS. 6 and 8.

Further, the optional isolation tube 306, which can insulate the anode lead 220 from the other sealing assembly 300 components, such as the metal plate 301, as well as from the casing 12 of the capacitor 10, has an inner diameter 309, wherein the inner diameter 309 defines an isolation tube orifice 326 through which the anode lead 220 can extend. The isolation tube 306 also has an upper end 329 and lower end 330.

The isolation tube orifice 326 as defined by the inner diameter 309 can have a diameter of from about 0.001 millimeters to about 3 millimeters, such as from about 0.005 millimeters to about 2.5 millimeters, such as from about 0.01 millimeters to about 2 millimeters so long as the anode lead 220 can extend through the isolation tube orifice 326 and maintain snug contact with the isolation tube 306 to ensure a tight seal. Further, the inner diameter 309 of the isolation tube 306 is generally constant throughout the length of the isolation tube 306 in the y-direction to maintain the snug contact with the anode lead 220 throughout the length of the isolation tube 306.

The various sealing assembly 300 components discussed above can be configured to receive the anode lead 220 of the capacitor 10 in such a manner to create a hermetic seal between the anode lead 220 and the casing 12 at the anode lead orifice 34. For instance, referring to FIGS. 6 and 8, the elastomeric ring 311 can be inserted into the metal housing 317 such that the lower surface 313 of the elastomeric ring 311 is in contact with the metal housing 317 towards its lower surface 319. Then, the metal plate 301 can be inserted into the metal housing 317 such that a lower surface 303 of the metal plate 301 is in contact with an upper surface 312 of the elastomeric ring 311. Thereafter, the sealing assembly 300 can be inserted or press fit into the anode lead orifice 34 in a sidewall 14 of the casing (see FIG. 1) from either outside the casing 12 or from an interior of the casing 13. Then, the anode lead 220 can be inserted through the cavity 328 of the metal housing 317, the elastomeric ring orifice 327, and the metal plate orifice 325.

Further, if an isolation tube 306 is utilized, the anode lead 220 can be first inserted through the isolation tube orifice 326 of the isolation tube 306, where the isolation tube orifice as defined by the isolation tube inner diameter 309 is just large enough to fit around the diameter 221 of the anode lead 220 and create a tight fit, after which the anode lead 220 and isolation tube 306 can be inserted through the cavity 328 of the metal housing 317, the elastomeric ring orifice 327, and the metal plate orifice 325, where the isolation tube 306 can have a first portion that extends outside the exterior of the side wall 20 of the first casing member 12 and a second portion that extends into the interior 13 of the casing 12 at the elastomeric ring 311. In the alternative, the isolation tube 306 can be inserted through the orifices of the sealing assembly 300 prior to insertion of the anode lead 220, after which the anode lead 220 can be inserted through the cavity 328 of the metal housing 317, the elastomeric ring orifice 327, and the metal plate orifice 325 as discussed above. In any event, the anode lead 220 and optional isolation tube 306 can extend from the exterior surface 27 of the sidewall 20 such that a first portion of the anode lead 220 and a first portion of the isolation tube 306 extend beyond the exterior surface 27 of the sidewall 20, while a second portion of the anode lead 220 and a second portion of the isolation tube 306 remain inside the casing, where the isolation tube 306 can generally act as a sleeve that fits snugly around the anode lead 220.

Figure 9:
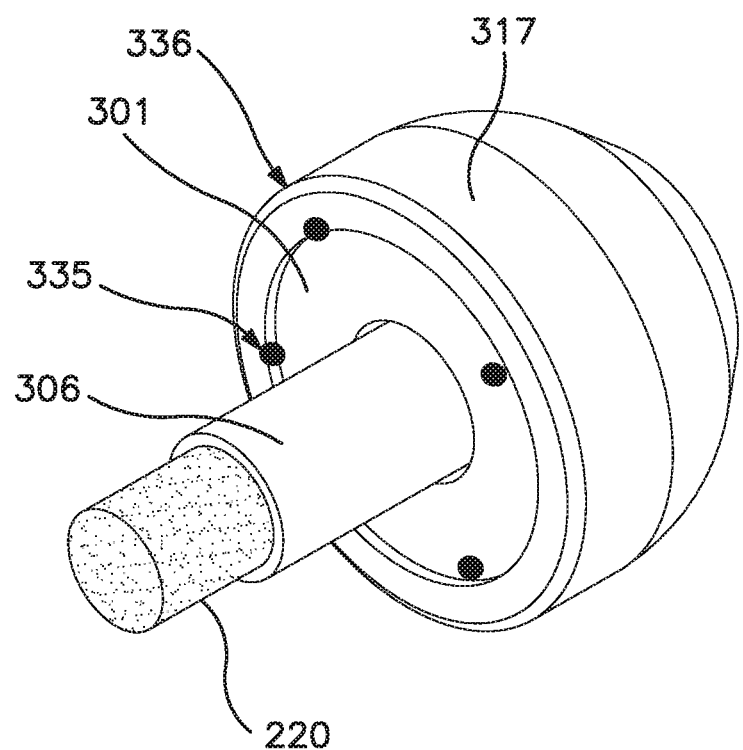
FIG. 9 is an assembled perspective view of the sealing assembly of FIGS. 5-7 showing where the assembly is welded during capacitor assembly.
Figure 10:
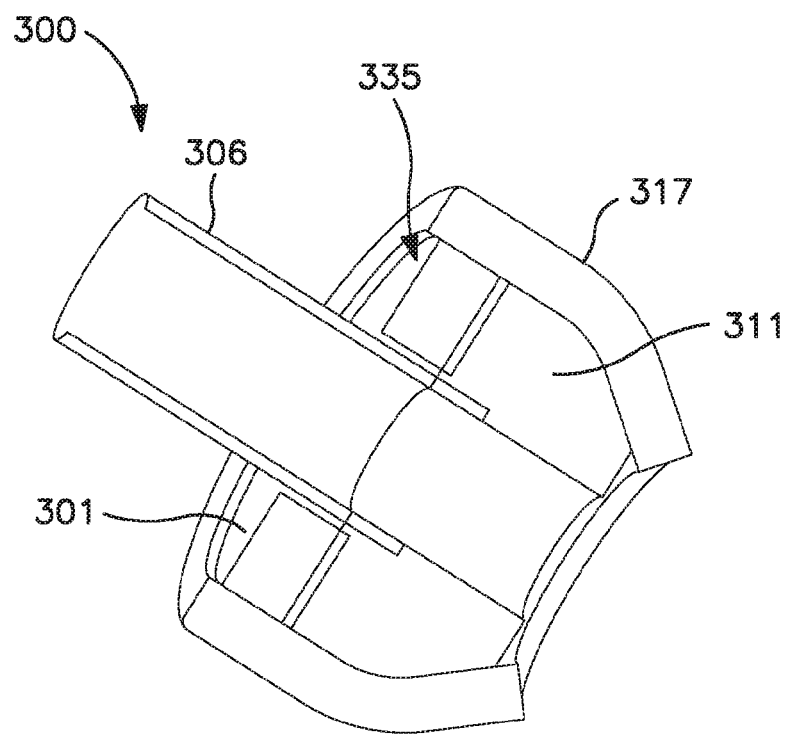
FIG. 10 is an assembled cross-sectional perspective view of the sealing assembly of FIGS. 5-7 showing where the metal plate is welded to the elastomeric ring.
Figure 11:
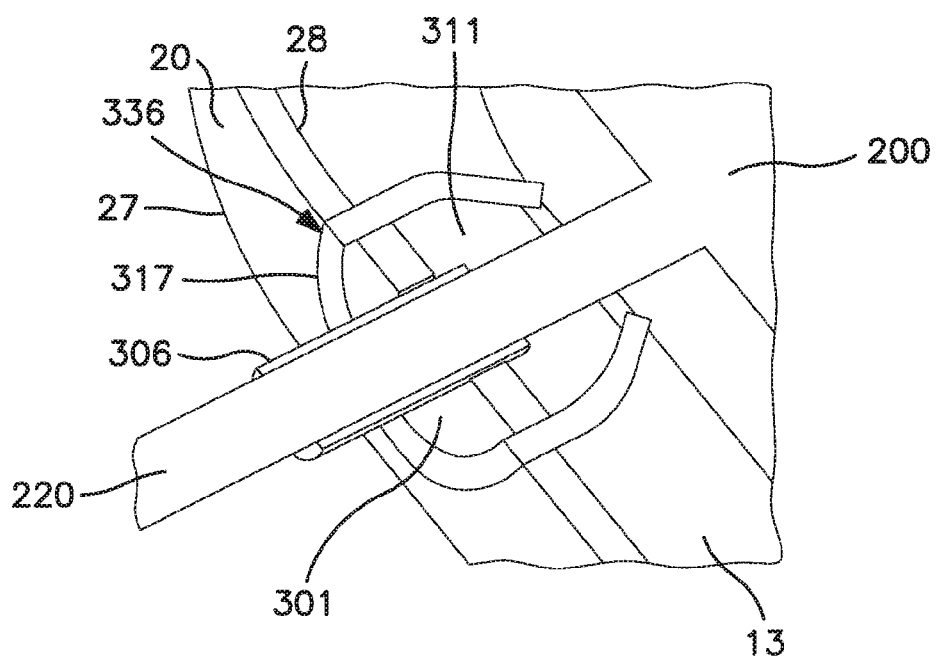
FIG. 11 is an assembled cross-sectional perspective view of the sealing assembly of FIGS. 5-7 showing where the metal housing is welded to the casing.

Regardless of the particular manner in which the sealing assembly 300 is inserted into the anode lead orifice 34, after the sealing assembly 300 is in place and after the anode lead 220 has been inserted through the sealing assembly 300 and appropriately positioned, the metal plate 301 and the elastomeric ring 311 can be welded together, as can the metal housing 301 and the first casing member 14 to ensure that the anode lead 220 is hermetically sealed at the anode lead orifice. Referring to FIGS. 9-11, the locations for the various weld points are shown. For instance, as shown in FIG. 9, the metal plate 301 can be welded, such as via laser welding or spot welding, around its circumference, where the welding at weld area 335 ensures an effective seal between the metal plate 301 and the elastomeric ring 311 (not shown). FIG. 10 is a cross-sectional perspective view showing weld area 335, where the metal plate 301 can be welded to the elastomeric ring 311 to create an effective seal of the anode lead 220 at the anode lead orifice 34. Meanwhile, the metal housing 317 can be welded, such as via laser welding or spot welding, around its circumference at weld area 336 to ensure an effective seal between the metal housing 317 and the side wall 20 of first casing member 14. FIG. 11 is a cross-sectional perspective view showing weld area 336, where the metal housing 317 can be welded to the side wall 20 of first casing member 14 at an upper surface 27 of the side wall 20. The overall effect of sealing the metal plate 301 to the elastomeric ring 311 and the metal housing 317 to the side wall 20 is to create a hermetic seal that is generally free of glass and can create a more effective seal compared to glass to metal seals.

The components of the sealing assembly 300 discussed above can be made from any material so long as an effective hermetic seal can be formed. For instance, the metal plate 301 and the optional metal housing 317 may be formed from a conductive material, such as a metal. For instance, the metal plate 301 and the optional metal housing 317 can be made of tantalum, niobium, aluminum, nickel, hafnium, titanium, copper, silver, steel (e.g., stainless), alloys thereof (e.g., electrically conductive oxides), composites thereof (e.g., metal coated with electrically conductive oxide), and so forth. In one particular embodiment, the metal plate 301 and the metal housing 317 can include titanium.

Meanwhile, the isolation tube 306 can be made of any suitable insulative material. For example, the insulative material may have an electrical resistance of about $1 \times 10^2$ ohms-m or more, in some embodiments about $1 \times 10^5$ ohms-m or more, and in some embodiments, from about $1 \times 10^{15}$ to about $1 \times 10^{25}$ ohms-m, determined at a temperature of 20° C. For example, glass materials may be employed as an insulative material, such as glass compositions containing CaO, $Al_2O_3$, $B_2O_3$, SrO, BaO, $LiO_2$, $SiO_2$, $TiO_2$, $Na_2O$, combinations thereof, etc. Barium lanthanoborate glass compositions, which contain boron oxide ($B_2O_3$), barium oxide (BaO), lanthanum oxide ($LiO_2$) and optionally at least one other oxide, are particularly suitable. Such compositions may be described in more detail in U.S. Pat. Nos. 5,648,302 and 5,104,738 to Brow, et al. Still other insulative materials may include polymer materials, such as fluoropolymers (e.g., polytetrafluoroethylene ("PTFE"), perfluoroalkylvinyl ether ("PVE"), poly(tetrafluoroethylene-co-perfluoroalkyvinyl ether) ("PFA"), fluorinated ethylene-propylene copolymer ("FEP"), ethylene-tetrafluoroethylene copolymer ("ETFE"), polyvinylidene fluoride ("PVDF"), polychlorotrifluoroethylene ("PCTFE"), and TEE copolymers with VF2 and/or HFP, etc.); polyvinyl chloride ("PVC"), polysulfones (e.g., polysulfone, polyethersulfone, etc.); polyimides (e.g., polyetherimide); polyolefins (e.g., polyethylene, polypropylene, etc.); and so forth, as well as mixtures thereof.

Further, the elastomeric ring 311 can be made of any suitable elastomer. For instance, the elastomeric ring 311 can be from an elastomer that is resistant to corrosion by the electrolyte (discussed below) and has sufficient dielectric strength to withstand the maximum voltage generated by the capacitor. In one embodiment, the elastomer can perform over a temperature range of about −55° C. to about 200° C. without degradation or loss of elasticity. Examples of elastomers that may be employed include butyl rubber, chlorobutyl rubber, ethylene propylene rubber (EPR), ethylene propylene diene rubber (EPDM), fluoroelastomers, such as VITON™, polytetrafluoroethylene, polychloroprene rubber, butadiene rubber, nitrile rubber, isoprene rubber, silicone rubber, and styrene butadiene rubber.

The sealing assembly of the present invention, such as described above, may generally be incorporated into a wet electrolytic capacitor using any of a variety of techniques known in the art. In this regard, the various additional components of the wet electrolytic capacitor will be discussed in more detail with reference to FIGS. 1-4.

II. Planar Anode

The planar anode is typically formed from a valve metal composition. The specific charge of the composition may vary, such as from about 2,000 μF*V/g to about 80,000 μF*V/g, in some embodiments from about 5,000 μF*V/g to about 40,000 μF*V/g or more, and in some embodiments, from about 10,000 to about 20,000 μF*V/g. The valve metal composition contains a valve metal (i.e., metal that is capable of oxidation) or valve metal-based compound, such as tantalum, niobium, aluminum, hafnium, titanium, alloys thereof, oxides thereof, nitrides thereof, and so forth. For example, the valve metal composition may contain an electrically conductive oxide of niobium, such as niobium oxide having an atomic ratio of niobium to oxygen of 1:1.0±1.0, in some embodiments 1:1.0±0.3, in some embodiments 1:1.0±0.1, and in some embodiments, 1:1.0±0.05. The niobium oxide may be $NbO_{0.7}$, $NbO_{1.0}$, $NbO_{1.1}$, and $NbO_2$. Examples of such valve metal oxides are described in U.S. Pat. No. 6,322,912 to Fife; U.S. Pat. No. 6,391,275 to Fife et al.; U.S. Pat. No. 6,416,730 to Fife et al.; U.S. Pat. No. 6,527,937 to Fife; U.S. Pat. No. 6,576,099 to Kimmel, et al.; U.S. Pat. No. 6,592,740 to Fife, et al.; and U.S. Pat. No. 6,639,787 to Kimmel, et al.; and U.S. Pat. No. 7,220,397 to Kimmel, et al., as well as U.S. Patent Application Publication Nos. 2005/0019581 to Schnitter, 2005/0103638 to Schnitter, et al.; 2005/0013765 to Thomas, et al.

To form the planar anode, a powder of the valve metal composition is generally employed. The powder may contain particles any of a variety of shapes, such as nodular, angular, flake, etc., as well as mixtures thereof. Particularly suitable powders are tantalum powders available from Cabot Corp. (e.g., C255 flake powder, TU4D flake/nodular powder, etc.) and H. C. Starck (e.g., NH175 nodular powder). The valve metal composition may be formed using techniques known to those skilled in the art. A precursor tantalum powder, for instance, may be formed by reducing a tantalum salt (e.g., potassium fluotantalate ($K_2TaF_7$), sodium fluotantalate ($Na_2TaF_7$), tantalum pentachloride ($TaCl_5$), etc.) with a reducing agent (e.g., hydrogen, sodium, potassium, magnesium, calcium, etc.).

Regardless of the particular method employed, the resulting powder may possess certain characteristics that enhance its ability to be formed into a capacitor anode. For example, the particles employed in the anode may be generally flat. The degree of flatness is generally defined by the "aspect ratio", i.e., the average diameter or width of the particles divided by the average thickness ("D/T"). For example, the aspect ratio of the particles may be from about 2 to about 100, in some embodiments from about 3 to about 50, in some embodiments, from about 4 to about 30. The particles may also have a specific surface area of from about 0.5 to about 10.0 m$^2$/g, in some embodiments from about 0.7 to about 5.0 m$^2$/g, and in some embodiments, from about 1.0 to about 4.0 m$^2$/g. The term "specific surface area" is defined in more detail above. The bulk density (also known as Scott density) is also typically from about 0.1 to about 2 grams per cubic centimeter (g/cm$^3$), in some embodiments from about 0.2 g/cm$^3$ to about 1.5 g/cm$^3$, and in some embodiments, from about 0.4 g/cm$^3$ to about 1 g/cm$^3$. "Bulk density" may be determined using a flow meter funnel and density cup. More specifically, the sample may be poured through the funnel into the cup until the sample completely fills and overflows the periphery of the cup, and thereafter sample may be leveled-off by a spatula, without jarring, so that it is flush with the top of the cup. The leveled sample is transferred to a balance and weighed to the nearest 0.1 gram to determine the density value. Such an apparatus is commercially available from Alcan Aluminum Corp. of Elizabeth, N.J. The particles may also have an average size (e.g., width) of from about 0.1 to about 100 micrometers, in some embodiments from about 0.5 to about 70 micrometers, and in some embodiments, from about 1 to about 50 micrometers.

To facilitate the construction of the planar anode, certain additional components may also be included in the powder. For example, the powder may be optionally mixed with a binder and/or lubricant to ensure that the particles adequately adhere to each other when pressed to form the planar anode body. Suitable binders may include, for instance, poly(vinyl butyral); poly(vinyl acetate); poly(vinyl alcohol); poly(vinyl pyrollidone); cellulosic polymers, such as carboxymethylcellulose, methyl cellulose, ethyl cellulose, hydroxyethyl cellulose, and methylhydroxyethyl cellulose; atactic polypropylene, polyethylene; polyethylene glycol (e.g., Carbowax from Dow Chemical Co.); polystyrene, poly(butadiene/styrene); polyamides, polyimides, and polyacrylamides, high molecular weight polyethers; copolymers of ethylene oxide and propylene oxide; fluoropolymers, such as polytetrafluoroethylene, polyvinylidene fluoride, and fluoro-olefin copolymers; acrylic polymers, such as sodium polyacrylate, poly(lower alkyl acrylates), poly (lower alkyl methacrylates) and copolymers of lower alkyl acrylates and methacrylates; and fatty acids and waxes, such as stearic and other soapy fatty acids, vegetable wax, microwaxes (purified paraffins), etc. The binder may be dissolved and dispersed in a solvent. Exemplary solvents may include water, alcohols, and so forth. When utilized, the percentage of binders and/or lubricants may vary from about 0.1% to about 8% by weight of the total mass. It should be understood, however, that binders and/or lubricants are not necessarily required in the present invention.

The resulting powder may be compacted to form a pellet using any conventional powder press device. For example, a press mold may be employed that is a single station compaction press containing a die and one or multiple punches. Alternatively, anvil-type compaction press molds may be used that use only a die and single lower punch. Single station compaction press molds are available in several basic types, such as cam, toggle/knuckle and eccentric/crank presses with varying capabilities, such as single action, double action, floating die, movable platen, opposed ram, screw, impact, hot pressing, coining or sizing. The powder may be compacted around an anode lead, such as an anode lead wire. The anode lead may be formed from any electrically conductive material, such as tantalum, niobium, aluminum, hafnium, titanium, etc., as well as electrically conductive oxides and/or nitrides of thereof. Further, the anode lead can have a diameter of from about 0.001 millimeters to about 3 millimeters, such as from about 0.005 millimeters to about 2.5 millimeters, such as from about 0.01 millimeters to about 2 millimeters.

Any binder/lubricant may be removed after pressing by heating the pellet under vacuum at a certain temperature (e.g., from about 150° C. to about 500° C.) for several minutes. Alternatively, the binder/lubricant may also be removed by contacting the pellet with an aqueous solution, such as described in U.S. Pat. No. 6,197,252 to Bishop, et al. Thereafter, the pellet is sintered to form a porous, integral mass. The present inventors have discovered that certain sintering conditions can result in an increase in the specific charge of the resulting planar anode, as well increase in the breakdown voltage of the resulting capacitor. More particularly, the pellet is typically sintered at a temperature of from about 800° C. to about 2000° C., in some embodiments from about 1200° C. to about 1800° C., and in some embodiments, from about 1500° C. to about 1700° C., for a time of from about 5 minutes to about 100 minutes, and in some embodiments, from about 8 minutes to about 15 minutes. This may occur in one or more steps. If desired, sintering may occur in an atmosphere that limits the transfer of oxygen atoms to the planar anode. For example, sintering may occur in a reducing atmosphere, such as in a vacuum, inert gas, hydrogen, etc. The reducing atmosphere may be at a pressure of from about 10 Torr to about 2000 Torr, in some embodiments from about 100 Torr to about 1000 Torr, and in some embodiments, from about 100 Torr to about 930 Torr. Mixtures of hydrogen and other gases (e.g., argon or nitrogen) may also be employed. When employed, flake particles may be better able to withstand the high sintering temperatures and prolonged sintering times often employed in forming the planar anode, and produce a porous sintered body with low shrinkage and a large specific surface area.

Upon sintering, the pellet shrinks due to the growth of metallurgical bonds between the particles. Because shrinkage generally increases the density of the pellet, lower press densities ("green") may be employed to still achieve the desired target density. For example, the target density of the pellet after sintering is typically from about 5 to about 8 grams per cubic centimeter. As a result of the shrinking phenomenon, however, the pellet need not be pressed to such high densities, but may instead be pressed to densities of less than about 6.0 grams per cubic centimeter, and in some embodiments, from about 4.5 to about 5.5 grams per cubic centimeter. Among other things, the ability to employ lower green densities may provide significant cost savings and increase processing efficiency. It should be understood that the pressed density may not always be uniform across the pellet, particularly if compression occurs in a direction perpendicular to the longitudinal axis of the wire. Namely, the pressed density is determined by dividing the amount of material by the volume of the pressed pellet. The volume of the pellet is directly proportional to the compressed length in the direction perpendicular to the longitudinal axis of the wire. The density is inversely proportional to the compressed length. Thus, the compressed length is actually lower at those locations adjacent to the wire than the remaining locations of the pellet. The pressed density is likewise greater at those locations adjacent to the wire. For example, the density of the pellet at those locations adjacent to the wire is typically at least about 10% greater, and in some cases, at least about 20% greater than the pressed density of the pellet at the remaining locations of the pellet.

Figure 2:
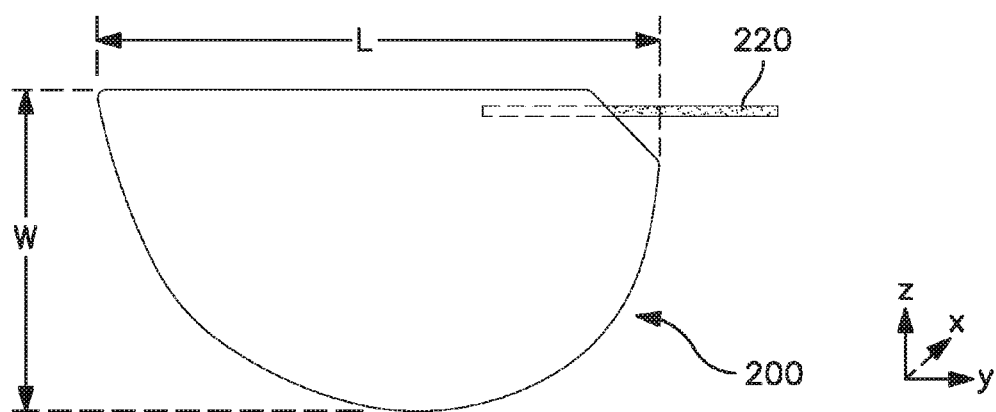
FIG. 2 is a top view of embodiment of an anode that may be employed in the capacitor of the present invention.
Figure 3:
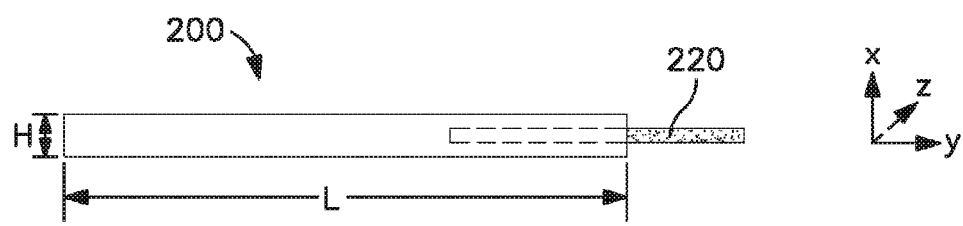
FIG. 3 is a frontal view of the anode of FIG. 2.

Referring to FIGS. 2-3, for example, one embodiment of a planar anode 200 is shown that contains an anode wire 220. The anode wire extends in a longitudinal direction ("y" direction) from the planar anode 200. In order to embed the anode wire 220 into the planar anode 200, a press mold may be partially filled with the powder, and then an anode wire may be inserted into the press mold. Thereafter, the mold may be filled with powder and the entire assembly compressed into a pellet.

The resulting planar anode can have a small overall thickness as compared to its overall length and overall width to improve the electrical performance and volumetric efficiency of the resulting capacitor. Referring to FIG. 2, for example, the length "L" represents the entire length of the anode 200 from a first end 60 to a second end 62. In certain cases, the length "L" of the anode 200 may range from about 1 millimeter to about 80 millimeters, such as from about 10 millimeters to about 60 millimeters, such as from about 20 millimeters to about 50 millimeters. Meanwhile, also referring to FIG. 2, the width "W" of the anode may also be from about 0.5 millimeters to about 60 millimeters, such as from about 1 millimeter to about 40 millimeters, such as from about 5 millimeters to about 30 millimeters. Further, referring to FIG. 3, typically, the thickness "H" of the anode is about 5 millimeters or less, such as from about 0.05 millimeters to about 4 millimeters, such as from about 0.1 millimeters to about 3.5 millimeters, such as from about 0.2 millimeters to about 2 millimeters. Generally, in some embodiments, the ratio of the length "L" of the anode to the thickness "H" of the planar anode can range from about 5 to about 50, in some embodiments from about 6 to about 40, and in some embodiments, from about 7 to about 30. Further, the ratio of the width "W" of the anode to the thickness "H" of the anode can range from about 4 to about 35, in some embodiments from about 5 to about 25, and in some embodiments, from about 6 to about 20.

In addition, although shown as a "D-shape" in FIG. 2, it should also be understood that the planar anode may possess any other desired shape, such as square, rectangular, circular, oval, triangular, etc. Polygonal shapes having more than four (4) edges (e.g., hexagon, octagon, heptagon, pentagon, etc.) may be particularly desired due to their relatively high surface area. Further, referring to FIGS. 1 and 4, for example, one embodiment of a capacitor 10 is shown that includes the planar anode 200 shown in FIGS. 2-3. Although only one planar anode is shown, it should be understood that multiple anodes (e.g., stack) may be employed as described, for instance, in U.S. Pat. No. 7,483,260 to Ziarniak, et al.

Moreover, regardless of the particular geometry of the planar anode, the planar anode also contains a dielectric formed by anodically oxidizing ("anodizing") the sintered anode so that a dielectric layer is formed over and/or within the planar anode. For example, a tantalum (Ta) anode may be anodized to tantalum pentoxide ($Ta_2O_5$). Typically, anodization is performed by initially applying a solution to the anode, such as by dipping anode into the electrolyte. Aqueous solvents (e.g., water) and/or non-aqueous solvents (e.g., ethylene glycol) may be employed. To enhance conductivity, a compound may be employed that is capable of dissociating in the solvent to form ions. Examples of such compounds include, for instance, acids, such as described below with respect to the electrolyte. For example, an acid (e.g., phosphoric acid) may constitute from about 0.01 wt. % to about 5 wt. %, in some embodiments from about 0.05 wt. % to about 0.8 wt. %, and in some embodiments, from about 0.1 wt. % to about 0.5 wt. % of the anodizing solution. If desired, blends of acids may also be employed.

A current is passed through the anodizing solution to form the dielectric layer. The value of the formation voltage manages the thickness of the dielectric layer. For example, the power supply may be initially set up at a galvanostatic mode until the required voltage is reached. Thereafter, the power supply may be switched to a potentiostatic mode to ensure that the desired dielectric thickness is formed over the entire surface of the anode. Of course, other known methods may also be employed, such as pulse or step potentiostatic methods. The temperature of the anodizing solution may range from about 10° C. to about 200° C., in some embodiments from about 20° C. to about 150° C., and in some embodiments, from about 30° C. to about 100° C. The resulting dielectric layer may be formed on a surface of the anode and within its pores. When employed, the specific nature of the powder may allow the resulting anode to achieve a high specific charge even at the high formation voltages often employed in the present invention. For example, within the ranges noted above, the anode may still be able to a specific charge of from about 2,000 μF*V/g to about 20,000 μF*V/g, in some embodiments from about 5,000 μF*V/g to about 15,000 μF*V/g or more, and in some embodiments, from about 8,000 to about 12,000 μF*V/g.

III. Cathode

In addition to the sealing assembly and the planar anode, a cathode is also employed in the capacitor that may be constructed using any of a variety of techniques. In one embodiment, the cathode contains a metal substrate, which may include any metal, such as tantalum, niobium, aluminum, nickel, hafnium, titanium, copper, silver, steel (e.g., stainless), alloys thereof (e.g., electrically conductive oxides), composites thereof (e.g., metal coated with electrically conductive oxide), and so forth, that is coated with an electrochemically-active material. Titanium and tantalum, as well as alloys thereof, are particularly suitable for use in the present invention. The geometric configuration of the substrate may generally vary as is well known to those skilled in the art, such as in the form of a container, can, foil, sheet, screen, mesh, etc. Although not required, in one embodiment, for example, the metal substrate can form the capacitor casing in which the planar anode is disclosed, and such casing can have a D-shape or any other shape that generally corresponds to the shape of the planar anode. For instance, it should be understood that any geometric configuration may be employed in the present invention, such as cylindrical, rectangular, triangular, prismatic, etc.

The substrate may be roughened to increase its surface area and increase the degree to which an electrochemically-active material may be able to adhere thereto. In one embodiment, for example, the surface is chemically etched, such as by applying a solution of a corrosive substance (e.g., hydrochloric acid) to the surface. The surface may also be electrochemically etched, such as by applying a voltage to a solution of the corrosive substance so that it undergoes electrolysis. The voltage may be raised to a sufficiently high level to initiate "sparking" at the surface of the substrate, which is believed to create high local surface temperatures sufficient that etches away the substrate. This technique is described in more detail in U.S. Pat. No. 8,279,585 to Dreissig, et al., which is incorporated herein in its entirety by reference thereto for all purposes. In addition to chemical or electrochemical roughening techniques, mechanical roughening may also be employed. In one embodiment, for instance, the surface of the metal substrate may be abrasive blasted by propelling a stream of abrasive media (e.g., sand) against at least a portion of a surface thereof.

An electrochemically-active material may also be applied to the cathode substrate to inhibit corrosion and also act as a heat barrier when voltage is increased. The electrochemically-active material may be formed from one or more layers. The material employed in such layer(s) may vary. Any of a variety of known electrochemically-active materials may generally be employed. One suitable material is a conductive polymer, such as those that are π-conjugated and have electrical conductivity after oxidation or reduction (e.g., electrical conductivity of at least about 1 μS cm$^{-1}$ after oxidation). Examples of such π-conjugated conductive polymers include, for instance, polyheterocycles (e.g., polypyrroles, polythiophenes, polyanilines, etc.), polyacetylenes, poly-p-phenylenes, polyphenolates, and so forth.

Substituted polythiophenes are particularly suitable for use as conductive polymer in that they have particularly good mechanical robustness and electrical performance. Without intending to be limited by theory, it is believed that charging of the capacitor to a high voltage (e.g., greater than the formation voltage) forces ions of the electrolyte into coatings containing such substituted polythiophenes. This causes the conductive polymer to "swell" and retain the ions near the surface, thereby enhancing charge density. Because the polymer is generally amorphous and non-crystalline, it can also dissipate and/or absorb the heat associated with the high voltage. Upon discharge, it is also believed that the substituted polythiophene "relaxes" and allows ions in the electrolyte to move out of the coating. Through such swelling and relaxation mechanism, charge density near the metal substrate can be increased without a chemical reaction with the electrolyte. Accordingly, mechanical robustness and good electrical performance may be provided without the need for conventional conductive coatings, such as those made from activated carbon or metal oxides (e.g., ruthenium oxide). In fact, excellent results may be achieved using the coating as the principal material on the metal substrate. That is, the coating may constitute at least about 90 wt. %, in some embodiments at least about 92 wt. %, and in some embodiments, at least about 95 wt. % of the material(s) present on the metal substrate. Nevertheless, it should be understood that other conductive coatings may also be used in some embodiments of the present invention.

In one particular embodiment, the substituted polythiophene has the following general structure:

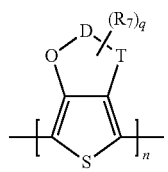

wherein,

T is O or S;

D is an optionally substituted $C_1$ to $C_5$ alkylene radical (e.g., methylene, ethylene, n-propylene, n-butylene, n-pentylene, etc.);

$R_7$ is a linear or branched, optionally substituted $C_1$ to $C_{18}$ alkyl radical (e.g., methyl, ethyl, n- or iso-propyl, n-, iso-, sec- or tert-butyl, n-pentyl, 1-methylbutyl, 2-methylbutyl, 3-methylbutyl, 1-ethylpropyl, 1,1-dimethylpropyl, 1,2-dimethylpropyl, 2,2-dimethylpropyl, n-hexyl, n-heptyl, n-octyl, 2-ethylhexyl, n-nonyl, n-decyl, n-undecyl, n-dodecyl, n-tridecyl, n-tetradecyl, n-hexadecyl, n-octadecyl, etc.); optionally substituted $C_5$ to $C_{12}$ cycloalkyl radical (e.g., cyclopentyl, cyclohexyl, cycloheptyl, cyclooctyl, cyclononyl cyclodecyl, etc.); optionally substituted $C_6$ to $C_{14}$ aryl radical (e.g., phenyl, naphthyl, etc.); optionally substituted $C_7$ to $C_{18}$ aralkyl radical (e.g., benzyl, o-, m-, p-tolyl, 2,3-, 2,4-, 2,5-, 2-6, 3-4-, 3,5-xylyl, mesityl, etc.); optionally substituted $C_1$ to $C_4$ hydroxyalkyl radical, or hydroxyl radical; and q is an integer from 0 to 8, in some embodiments, from 0 to 2, and in one embodiment, 0; and n is from 2 to 5,000, in some embodiments from 4 to 2,000, and in some embodiments, from 5 to 1,000. Example of substituents for the radicals "D" or "$R_7$" include, for instance, alkyl, cycloalkyl, aryl, aralkyl, alkoxy, halogen, ether, thioether, disulphide, sulfoxide, sulfone, sulfonate, amino, aldehyde, keto, carboxylic acid ester, carboxylic acid, carbonate, carboxylate, cyano, alkylsilane and alkoxysilane groups, carboxylamide groups, and so forth.

Particularly suitable thiophene polymers are those in which "D" is an optionally substituted $C_2$ to $C_3$ alkylene radical. For instance, the polymer may be optionally substituted poly(3,4-ethylenedioxythiophene), which has the following general structure:

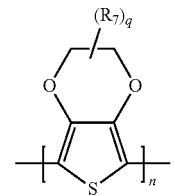

Methods for forming conductive polymers, such as described above, are well known in the art. For instance, U.S. Pat. No. 6,987,663 to Merker, et al. describes various techniques for forming substituted polythiophenes from a monomeric precursor. The monomeric precursor may, for instance, have the following structure:

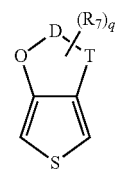

wherein,

T, D, $R_7$, and q are defined above. Particularly suitable thiophene monomers are those in which "D" is an optionally substituted $C_2$ to $C_3$ alkylene radical. For instance, optionally substituted 3,4-alkylenedioxythiophenes may be employed that have the general structure:

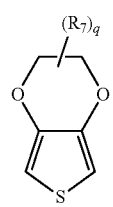

wherein, $R_7$ and q are as defined above. In one particular embodiment, "q" is 0. One commercially suitable example of 3,4-ethylenedioxythiophene is available from Heraeus Clevios under the designation Clevios™ M. Other suitable monomers are also described in U.S. Pat. No. 5,111,327 to Blohm, et al. and U.S. Pat. No. 6,635,729 to Groenendaal, et al. Derivatives of these monomers may also be employed that are, for example, dimers or trimers of the above monomers. Higher molecular derivatives, i.e., tetramers, pentamers, etc. of the monomers are suitable for use in the present invention. The derivatives may be made up of identical or different monomer units and used in pure form and in a mixture with one another and/or with the monomers. Oxidized or reduced forms of these precursors may also be employed.

The thiophene monomers may be chemically polymerized in the presence of an oxidative catalyst. The oxidative catalyst typically includes a transition metal cation, such as iron(III), copper(II), chromium(VI), cerium(IV), manganese (IV), manganese(VII), ruthenium(III) cations, etc. A dopant may also be employed to provide excess charge to the conductive polymer and stabilize the conductivity of the polymer. The dopant typically includes an inorganic or organic anion, such as an ion of a sulfonic acid. In certain embodiments, the oxidative catalyst employed in the precursor solution has both a catalytic and doping functionality in that it includes a cation (e.g., transition metal) and anion (e.g., sulfonic acid). For example, the oxidative catalyst may be a transition metal salt that includes iron(III) cations, such as iron(III) halides (e.g., $FeCl_3$) or iron(III) salts of other inorganic acids, such as $Fe(ClO_4)_3$ or $Fe_2(SO_4)_3$ and the iron(III) salts of organic acids and inorganic acids comprising organic radicals. Examples of iron (III) salts of inorganic acids with organic radicals include, for instance, iron(III) salts of sulfuric acid monoesters of $C_1$ to $C_{20}$ alkanols (e.g., iron(III) salt of lauryl sulfate). Likewise, examples of iron (III) salts of organic acids include, for instance, iron(III) salts of $C_1$ to $C_{20}$ alkane sulfonic acids (e.g., methane, ethane, propane, butane, or dodecane sulfonic acid); iron (III) salts of aliphatic perfluorosulfonic acids (e.g., trifluoromethane sulfonic acid, perfluorobutane sulfonic acid, or perfluorooctane sulfonic acid); iron (III) salts of aliphatic $C_1$ to $C_{20}$ carboxylic acids (e.g., 2-ethylhexylcarboxylic acid); iron (III) salts of aliphatic perfluorocarboxylic acids (e.g., trifluoroacetic acid or perfluorooctane acid); iron (III) salts of aromatic sulfonic acids optionally substituted by $C_1$ to $C_{20}$ alkyl groups (e.g., benzene sulfonic acid, o-toluene sulfonic acid, p-toluene sulfonic acid, or dodecylbenzene sulfonic acid); iron (III) salts of cycloalkane sulfonic acids (e.g., camphor sulfonic acid); and so forth. Mixtures of these above-mentioned iron(III) salts may also be used. Iron(III)-p-toluene sulfonate, iron(III)-o-toluene sulfonate, and mixtures thereof, are particularly suitable. One commercially suitable example of iron(III)-p-toluene sulfonate is available from Heraeus Clevios under the designation Clevios™ C.

Various methods may be utilized to form a conductive polymer layer. In one embodiment, the oxidative catalyst and monomer are applied, either sequentially or together, such that the polymerization reaction occurs in situ on the substrate. Suitable application techniques may include screen-printing, dipping, electrophoretic coating, and spraying, may be used to form a conductive polymer coating. As an example, the monomer may initially be mixed with the oxidative catalyst to form a precursor solution. Once the mixture is formed, it may be applied to the substrate and then allowed to polymerize so that the conductive coating is formed on the surface. Alternatively, the oxidative catalyst and monomer may be applied sequentially. In one embodiment, for example, the oxidative catalyst is dissolved in an organic solvent (e.g., butanol) and then applied as a dipping solution. The substrate may then be dried to remove the solvent therefrom. Thereafter, the substrate may be dipped into a solution containing the monomer. Polymerization is typically performed at temperatures of from about −10° C. to about 250° C., and in some embodiments, from about 0° C. to about 200° C., depending on the oxidizing agent used and desired reaction time. Suitable polymerization techniques, such as described above, may be described in more detail in U.S. Pat. No. 7,515,396 to Biler. Still other methods for applying such conductive coating(s) may be described in U.S. Pat. No. 5,457,862 to Sakata, et al., U.S. Pat. No. 5,473,503 to Sakata, et al., U.S. Pat. No. 5,729,428 to Sakata, et al., and U.S. Pat. No. 5,812,367 to Kudoh, et al.

In addition to in situ application, a conductive polymer layer may also be applied in the form of a dispersion of conductive polymer particles. Although their size may vary, it is typically desired that the particles possess a small diameter to increase the surface area available for adhering to the substrate. For example, the particles may have an average diameter of from about 1 to about 500 nanometers, in some embodiments from about 5 to about 400 nanometers, and in some embodiments, from about 10 to about 300 nanometers. The $D_{90}$ value of the particles (particles having a diameter of less than or equal to the $D_{90}$ value constitute 90% of the total volume of all of the solid particles) may be about 15 micrometers or less, in some embodiments about 10 micrometers or less, and in some embodiments, from about 1 nanometer to about 8 micrometers. The diameter of the particles may be determined using known techniques, such as by ultracentrifuge, laser diffraction, etc.

If desired, one or more of the above-described application steps may be repeated until the desired thickness of the coating is achieved. In some embodiments, only a relatively thin layer of the coating is formed at a time. The total target thickness of the coating may generally vary depending on the desired properties of the capacitor. Typically, the resulting conductive polymer coating has a thickness of from about 0.2 micrometers ("μm") to about 50 μm, in some embodiments from about 0.5 μm to about 20 μm, and in some embodiments, from about 1 μm to about 5 μm. It should be understood that the thickness of the coating is not necessarily the same at all locations on the substrate. Nevertheless, the average thickness of the coating on the substrate generally falls within the ranges noted above.

The conductive polymer layer may optionally be healed. Healing may occur after each application of a conductive polymer layer or may occur after the application of the entire coating. In some embodiments, the conductive polymer can be healed by dipping the part into an electrolyte solution, and thereafter applying a constant voltage to the solution until the current is reduced to a preselected level. If desired, such healing can be accomplished in multiple steps. For example, an electrolyte solution can be a dilute solution of the monomer, the catalyst, and dopant in an alcohol solvent (e.g., ethanol). The coating may also be washed if desired to remove various byproducts, excess reagents, and so forth.

IV. Working Electrolyte

The capacitor also includes a working electrolyte (not shown) that can generally be in the form of a liquid, such as a solution (e.g., aqueous or non-aqueous), dispersion, gel, etc. The working electrolyte is disposed inside the casing and is the electrically active material that provides the connecting path between the planar anode and cathode. If desired, the planar anode may initially be impregnated with an electrolyte (not shown) before being positioned within a casing (discussed below). The electrolyte may also be added to the capacitor at a later stage of production. Various suitable electrolytes are described in U.S. Pat. Nos. 5,369, 547 and 6,594,140 to Evans, et al., which are incorporated herein their entirety by reference thereto for all purposes.

Typically, the electrolyte is ionically conductive in that has an ionic conductivity of from about 1 to about 100 milliSiemens per centimeter ("mS/cm"), in some embodiments from about 5 to about 80 mS/cm, in some embodiments from about 15 mS/cm to about 70 mS/cm, and in some embodiments, from about 20 to about 60 mS/cm, determined at a temperature of 25° C. using any known electric conductivity meter (e.g., Oakton Con Series 11). Within the ranges noted, the electric field is strong as the dielectric but can extend into the electrolyte to a length (Debye length) sufficient to result in significant charge separation. This extends the potential energy of the dielectric to the electrolyte so that the resulting capacitor is able to store even more potential energy than predicted by the thickness of the dielectric. In other words, the capacitor may be charged to a voltage that is close to or even exceeds the formation voltage of the dielectric. The ratio of the voltage to which the capacitor can be charged to the formation voltage may, for instance, be from about 0.80 to about 2.00, and in some embodiments, from about 0.85 to about 1.50, and in some embodiments, from about 0.86 to about 1.20. As an example, the voltage to which the capacitor is charged may be from about 150 volts to about 300 volts, in some embodiments from about 180 volts to about 260 volts, and in some embodiments, from about 200 volts to about 240 volts. The formation voltage may likewise range from about from about 180 volts to about 320 volts, in some embodiments from about 200 volts to about 280 volts, and in some embodiments, from about 220 volts to about 250 volts. The working electrolyte is also relatively neutral and thus has a pH value of from about 4.5 to about 8.0, in some embodiments from about 5.0 to about 7.5, in some embodiments, from about 5.5 to about 7.0, and in some embodiments from about 6.0 to about 6.5. Among other things, such a pH may enhance the ability of hydrogen ions present in an aqueous electrolyte to interact with the cathode material to achieve maximum capacitance and thus energy density.

The desired ionic conductivity may be achieved by selecting ionic compound(s) (e.g., acids, bases, salts, and so forth) within certain concentration ranges. In one particular embodiment, salts of weak organic acids may be effective in achieving the desired conductivity of the electrolyte. The cation of the salt may include monatomic cations, such as alkali metals (e.g., $Li^+$, $Na^+$, $K^+$, $Rb^+$, or $Cs^+$), alkaline earth metals (e.g., $Be^{2+}$, $Mg^{2+}$, $Ca^{2+}$, $Sr^{2+}$ or $Ba^{2+}$), transition metals (e.g., $Ag^+$, $Fe^{2+}$, $Fe^{3+}$, etc.), as well as polyatomic cations, such as $NH_4^+$. The monovalent ammonium ($NH_4$), sodium ($K^+$), and lithium ($Li^+$) are particularly suitable cations for use in the present invention. The organic acid used to form the anion of the salt is "weak" in the sense that it typically has a first acid dissociation constant ($pK_{a1}$) of about 0 to about 11, in some embodiments about 1 to about 10, and in some embodiments, from about 2 to about 10, determined at 25° C. Any suitable weak organic acids may be used in the present invention, such as carboxylic acids, such as acrylic acid, methacrylic acid, malonic acid, succinic acid, salicylic acid, sulfosalicylic acid, adipic acid, maleic acid, malic acid, oleic acid, gallic acid, tartaric acid (e.g., dextotartaric acid, mesotartaric acid, etc.), citric acid, formic acid, acetic acid, glycolic acid, oxalic acid, propionic acid, phthalic acid, isophthalic acid, glutaric acid, gluconic acid, lactic acid, aspartic acid, glutaminic acid, itaconic acid, trifluoroacetic acid, barbituric acid, cinnamic acid, benzoic acid, 4-hydroxybenzoic acid, aminobenzoic acid, etc.; blends thereof, and so forth. Polyprotic acids (e.g., diprotic, triprotic, etc.) are particularly desirable for use in forming the salt, such as adipic acid ($pK_{a1}$ of 4.43 and $pK_{a2}$ of 5.41), α-tartaric acid ($pK_{a1}$ of 2.98 and $pK_{a2}$ of 4.34), meso-tartaric acid ($pK_{a1}$ of 3.22 and $pK_{a2}$ of 4.82), oxalic acid ($pK_{a1}$ of 1.23 and $pK_{a2}$ of 4.19), lactic acid ($pK_{a1}$ of 3.13, $pK_{a2}$ of 4.76, and $pK_{a3}$ of 6.40), etc.

While the actual amounts may vary depending on the particular salt employed, its solubility in the solvent(s) used in the electrolyte, and the presence of other components, such weak organic acid salts are typically present in the electrolyte in an amount of from about 0.1 to about 40 wt. %, in some embodiments from about 0.2 to about 35 wt. %, in some embodiments from about 0.3 to about 30 wt. %, and in some embodiments, from about 0.5 to about 25 wt. %.

The electrolyte is typically aqueous in that it contains an aqueous solvent, such as water (e.g., deionized water). For example, water (e.g., deionized water) may constitute from about 20 wt. % to about 95 wt. %, in some embodiments from about 30 wt. % to about 90 wt. %, and in some embodiments, from about 40 wt. % to about 85 wt. % of the electrolyte. A secondary solvent may also be employed to form a solvent mixture. Suitable secondary solvents may include, for instance, glycols (e.g., ethylene glycol, propylene glycol, butylene glycol, triethylene glycol, hexylene glycol, polyethylene glycols, ethoxydiglycol, dipropyleneglycol, etc.); glycol ethers (e.g., methyl glycol ether, ethyl glycol ether, isopropyl glycol ether, etc.); alcohols (e.g., methanol, ethanol, n-propanol, iso-propanol, and butanol); ketones (e.g., acetone, methyl ethyl ketone, and methyl isobutyl ketone); esters (e.g., ethyl acetate, butyl acetate, diethylene glycol ether acetate, methoxypropyl acetate, ethylene carbonate, propylene carbonate, etc.); amides (e.g., dimethylformamide, dimethylacetamide, dimethylcaprylic/ capric fatty acid amide and N-alkylpyrrolidones); sulfoxides or sulfones (e.g., dimethyl sulfoxide (DMSO) and sulfolane); and so forth. Such mixtures typically contain water in an amount from about 40 wt. % to about 80 wt. %, in some embodiments from about 50 wt % to about 75 wt. %, and in some embodiments, from about 60 wt. % to about 70 wt. % of the solvent system and secondary solvents in an amount from about 20 wt. % to about 60 wt. %, in some embodiments from about 25 wt. % to about 50 wt. %, and in some embodiments, from about 30 wt. % to about 40 wt. % of the solvent system. Likewise, when such mixtures are employed, water typically constitutes from about 30 wt. % to about 70 wt. %, in some embodiments from about 35 wt. % to about 65 wt. %, and in some embodiments, from about 40 wt. % to about 60 wt. % of the electrolyte and secondary solvents may constitute from about 5 wt. % to about 40 wt. %, in some embodiments from about 10 wt % to about 35 wt. %, and in some embodiments, from about 15 wt. % to about 30 wt. % of the electrolyte.

One or more acids or pH adjusters are also employed to help achieve the desired pH and conductivity values. Suitable acids may include, for instance, inorganic acids, such as hydrochloric acid, nitric acid, sulfuric acid, phosphoric acid, polyphosphoric acid, boric acid, boronic acid, etc.; organic acids, including carboxylic acids, such as acrylic acid, methacrylic acid, malonic acid, succinic acid, salicylic acid, sulfosalicylic acid, adipic acid, maleic acid, malic acid, oleic acid, gallic acid, tartaric acid, citric acid, formic acid, acetic acid, ethylenediaminetetraacetic acid ("EDTA"), glycolic acid, oxalic acid, propionic acid, phthalic acid, isophthalic acid, glutaric acid, gluconic acid, lactic acid, aspartic acid, glutaminic acid, itaconic acid, trifluoroacetic acid, barbituric acid, cinnamic acid, benzoic acid, 4-hydroxybenzoic acid, aminobenzoic acid, etc.; sulfonic acids, such as methanesulfonic acid, benzenesulfonic acid, toluenesulfonic acid, trifluoromethanesulfonic acid, styrenesulfonic acid, naphthalene disulfonic acid, hydroxybenzenesulfonic acid, etc.; polymeric acids, such as poly(acrylic) or poly(methacrylic) acid and copolymers thereof (e.g., maleic-acrylic, sulfonic-acrylic, and styrene-acrylic copolymers), carageenic acid, carboxymethyl cellulose, alginic acid, etc.; and so forth. EDTA may be particularly suitable when a gelled electrolyte is used as it not only can reduce the pH value of the electrolyte, but it can also serve as a sequestering agent for any metallic impurities that may be present in the particles.

Although the total concentration of acids may vary, they are typically present in an amount of from about 0.01 wt. % to about 10 wt %, in some embodiments from about 0.05 wt. % to about 5 wt. %, and in some embodiments, from about 0.1 wt. % to about 2 wt. % of the electrolyte. In one particular embodiment, a mixture of different acids may be employed, such as mixture of an inorganic and an organic acid. In such embodiments, inorganic acids (e.g., phosphoric acid) may constitute from about 0.005 wt % to about 5 wt. %, in some embodiments from about 0.01 wt. % to about 3 wt. %, and in some embodiments, from about 0.05 wt. % to about 1 wt. % of the electrolyte, and organic acids (e.g., EDTA) may likewise constitute from about 0.005 wt. % to about 5 wt. %, in some embodiments from about 0.01 wt. % to about 3 wt. %, and in some embodiments from about 0.05 wt. % to about 1 wt. % of the electrolyte.

The electrolyte may also contain other components that help improve the electrical performance of the capacitor. For instance, a depolarizer may be employed in the electrolyte to help inhibit the evolution of hydrogen gas at the cathode of the electrolytic capacitor, which could otherwise cause the capacitor to bulge and eventually fail. When employed, the depolarizer normally constitutes from about 1 to about 500 parts per million ("ppm"), in some embodiments from about 10 to about 200 ppm, and in some embodiments, from about 20 to about 150 ppm of the electrolyte. For instance, the depolarizers normally constitute from about 0.01 wt. % to about 5 wt. %, in some embodiments from about 0.05 wt. % to about 2 wt. %, and in some embodiments, from about 0.1 wt. % to about 1 wt. % of the electrolyte.

Suitable depolarizers may include nitroaromatic compounds, such as 2-nitrophenol, 3-nitrophenol, 4-nitrophenol, 2-nitrobenzonic acid, 3-nitrobenzonic acid, 4-nitrobenzonic acid, 2-nitroacetophenone, 3-nitroacetophenone, 4-nitroacetophenone, 2-nitroanisole, 3-nitroanisole, 4-nitroanisole, 2-nitrobenzaldehyde, 3-nitrobenzaldehyde, 4-nitrobenzaldehyde, 2-nitrobenzyl alcohol, 3-nitrobenzyl alcohol, 4-nitrobenzyl alcohol, 2-nitrophthalic acid, 3-nitrophthalic acid, 4-nitrophthalic acid, and so forth. Particularly suitable nitroaromatic depolarizers for use in the present invention are nitrobenzoic acids, anhydrides or salts thereof, substituted with one or more alkyl groups (e.g., methyl, ethyl, propyl, butyl, etc). Specific examples of such alkyl-substituted nitrobenzoic compounds include, for instance, 2-methyl-3-nitrobenzoic acid; 2-methyl-6-nitrobenzoic acid; 3-methyl-2-nitrobenzoic acid; 3-methyl-4-nitrobenzoic acid; 3-methyl-6-nitrobenzoic acid; 4-methyl-3-nitrobenzoic acid; anhydrides or salts thereof; and so forth.

In one particular embodiment, the working electrolyte can be in the form of a viscoelastic "gel", which is generally defined as a solid or semi-solid colloidal suspension that contains a continuous phase and a dispersed phase, wherein at least one of the phases is a solid and at least one of the phases is a liquid. For example, a hydrogel may be formed when the inorganic oxide particles are crosslinked to form a continuous phase and the solvent contains water as a disperse phase that is entrapped within the crosslinked network. Regardless of its exact form, the viscoelastic gel within the capacitor is in the form of a semi-solid or solid so that it is not readily flowable at room temperature. This property can be represented by the viscoelastic phase angle δ, which is the degree to which the sinusoidal time variation in the stress is out of phase with the sinusoidal time variation in the shear rate. The phase angle δ for an ideal elastic solid is 0° (in phase) and the phase angle δ for an ideal viscous liquid is 90° (out of phase). In the present invention, the gelled electrolyte typically exhibits a phase angle δ of from 0° to about 20°, in some embodiments from 0,1° to about 5°, and in some embodiments, from about 0.2° to about 2°. Another parameter that can represent the viscoelastic behavior of the gel is the storage modulus, G', which is determined by dividing the "in-phase" component of the stress (representing solid-like behavior) by the maximum strain. Typically, the gelled electrolyte of the present invention exhibits a storage modulus of about 5 kilopascals ("kPa") or more, in some embodiments about 10 kPa or more, and in some embodiments from about 15 to about 50 kPa. The phase angle and storage modulus can be determined at room temperature (e.g., 25° C.) by dynamic oscillatory testing (e.g., frequency of 10 Hz and pressure of 5 Pa) with a rheometer having a cone plate configuration.

To achieve the combination of high conductivity and a neutral pH value, the gel working electrolyte can contain a combination of the weak organic acid salt, solvent system, and pH adjuster (acid) discussed above in conjunction with inorganic oxide particles to help achieve the desired viscosity and electrical properties for the capacitor. The amount of inorganic oxide particles in the electrolyte may vary depending on the degree of gelation required, as well as the particular nature and concentration of other components in the electrolyte. Typically, however, inorganic oxide particles constitute from about 0.5 wt. % to about 20 wt. %, in some embodiments from about 1 wt. % to about 15 wt. %, and in some embodiments, from about 1.5 wt. % to about 10 wt. % of the electrolyte.

The particles may possess various forms, shapes, and sizes depending upon the desired result. For instance, the particles may be in the shape of a sphere, crystal, rod, disk, tube, string, etc. The average size of the particles may be less than about 1,000 nanometers, in some embodiments from about 1 to about 500 nanometers, in some embodiments from about 2 to about 200 nanometers, and in some embodiments, from about 4 to about 50 nanometers. As used herein, the average size of a particle refers to its average length, width, height, and/or diameter. The particles also typically have a high specific surface area, such as from about 50 square meters per gram ($m^2/g$) to about 1000 $m^2/g$, in some embodiments from about 100 $m^2/g$ to about 600 $m^2/g$, and in some embodiments, from about 150 m²/g to about 400 m²/g. The term "specific surface area" generally refers to surface area as determined by the physical gas adsorption (B.E.T.) method of Bruanauer, Emmet, and Teller, Journal of American Chemical Society, Vol. 60, 1938, p. 309, with nitrogen as the adsorption gas. The test may be conducted with a MONOSORB® Specific Surface Area Analyzer available from QUANTACHROME Corporation, Syosset, N.Y., which measures the quantity of adsorbate nitrogen gas adsorbed on a solid surface by sensing the change in thermal conductivity of a flowing mixture of adsorbate and inert carrier gas (e.g., helium). In addition, the particles may also be relatively nonporous or solid. That is, the particles may have a pore volume that is less than about 0.5 milliliters per gram (ml/g), in some embodiments less than about 0.4 milliliters per gram, in some embodiments less than about 0.3 ml/g, and in some embodiments, from about 0.2 ml/g to about 0.3 ml/g. Without intending to be limited by theory, it is believed that particles having such a small size, high surface area, and solid nature may improve the gelation rate and enhance the uniformity and stability of the resulting suspension.

The inorganic oxide particles may be formed from a variety of materials, including, but not limited to, silica, alumina, zirconia, magnesium oxide, titanium dioxide, iron oxide, zinc oxide, copper oxide, etc., as well as combinations thereof. The particles may also be formed using a fumed process, precipitation, etc. Due to their higher surface area and smaller particle size, however, fumed particles are particularly suitable for use in the present invention. Fumed silica, for instance, is amorphous $SiO_2$ that can be produced by vapor phase hydrolysis of silicon tetrachloride in a hydrogen oxygen flame. Three-dimensional branched chain aggregates are produced in the flame from fusion of the primary particles. During cooling, these aggregates agglomerate into a fine powder having a particle size within the ranges noted above. Fumed silica possesses silanol groups that can react under acidic conditions to form a cross-linked network. The resulting siloxane cross-linkage is a compound of silicon and oxygen in which each atom of silicon is bonded to four oxygen atoms, forming a tetrahedral structure, in a manner analogous to the bonding of carbon to hydrogen in methane, the bonds being of about the same strength in each case. This structure is found in the dioxide and in silicates generally, where the $SiO_4$ groups occur in chains or rings. By creating siloxane cross-linkages, a gel is formed that entraps the liquid phase of the electrolyte. Commercially suitable fumed silica particles may, for instance, include those available from Cabot Corporation under the designation CAB-O-SIL®.

The components of the working electrolyte can be combined together in a variety of different ways, either before and/or after their incorporation into the capacitor. In one particular embodiment, the electrolyte may be gelled before it is placed into contact with the anode and/or cathode (discussed below). For example, when the components of the electrolyte are initially combined together, the electrolyte may be in the form of a sol that contains particles as a disperse phase. However, such sols can be catalyzed to induce gelation by several methods. Examples include adjusting the pH and/or temperature of the sol to a point where gelation occurs. Alternatively, the sol may be subjected to a controlled form of energy (e.g., heat, ultrasonic, ultraviolet light, electron beam radiation, etc.) to induce gelation. The use of ultrasonic energy (e.g., ultrasonic probes) is particularly desirable as it minimizes the need to alter the pH or temperature of the electrolyte.

The electrolyte can be incorporated into the capacitor in a variety of different ways. In one embodiment, for example, the electrolyte is simply added to the capacitor after the anode and cathode are positioned in the desired configuration. This may be accomplished, for instance, using a fill port. The anode may also be pre-impregnated with the electrolyte, such as by dipping the anode into the electrolyte before it is placed into the capacitor. Impregnation of the anode with the electrolyte can further enhance the degree of contact between the anode and the electrolyte. In either case, the electrolyte can have a low initial viscosity and flowability so that it can be precisely incorporated into the capacitor. For example, when a gel, the electrolyte may have an initial viscosity (e.g., 1 hour or less after gelation is initiated) within the range of from about 1 to about 40 centipoise, in some embodiments from about 2 to about 30 centipoise, and in some embodiments, from about 3 to about 10 centipoise, as determined using a Brookfield LVT viscometer (spindle #3 at 60 rpm) at a temperature of 25° C. Likewise, the gel may have an initial phase angle δ of from about 50° to 90°, in some embodiments from about 60° to 90°, and in some embodiments, from about 80° to 90°, as well as an initial storage modulus G' of about 1 kilopascal or less, in some embodiments about 0.1 kilopascals or less, and in some embodiments, from 0 to about 0.01 kilopascals.

After incorporation into the capacitor, however, the electrolyte may continue to gel until the viscosity is raised, such as to a viscosity, phase angle 5, and/or storage modulus G' within the target ranges noted above. This "semi-solid" or "solid" transition may occur relatively after gelation is induced, such as from about 1 to about 100 hours, in some embodiments from about 10 to about 80 hours, and in some embodiments, from about 20 to about 60 hours. The transition may also occur before and/or after the anode is incorporated into the capacitor and placed in contact with the cathode. If desired, an additional "fill" electrolyte may be added to ensure that good electrical contact exists between the impregnated anode and the cathode. This fill electrolyte may be formed in accordance with the present invention, or it may be formed from other known components.

Regardless of the particular characteristics of the sealing assembly, planar anode, cathode, and working electrolyte, the planar anode 200 and other components are generally positioned within an interior of a casing 12, a portion of which may also serve as the cathode for the capacitor. Further, electrochemically-active material (not shown) may be applied to at least a portion of the casing 12 to inhibit corrosion and also act as a heat barrier when voltage is increased. In one embodiment, at least a portion of the casing 12 is generally formed from a metal, which may include any metal, such as tantalum, niobium, aluminum, nickel, hafnium, titanium, copper, silver, steel (e.g., stainless), alloys thereof (e.g., electrically conductive oxides), composites thereof (e.g., metal coated with electrically conductive oxide), and so forth, that is coated with an electrochemically-active material (cathode). Titanium and tantalum, as well as alloys thereof, are particularly suitable for use in the present invention. In other embodiments, a portion of the casing may be formed from a non-metallic material. The geometric configuration of the substrate may generally vary as is well known to those skilled in the art, such as in the form of a container, casing, foil, sheet, screen, mesh, etc. In one embodiment, for example, the metal substrate forms a planar casing having a D-shape. It should be understood, however, that any geometric configuration may be employed in the present invention, such as square, circular, rectangular, triangular, prismatic, etc. The casing can also include a lid that covers the anode and electrolyte, which may be formed from the same or different material than the casing.

Figure 4:
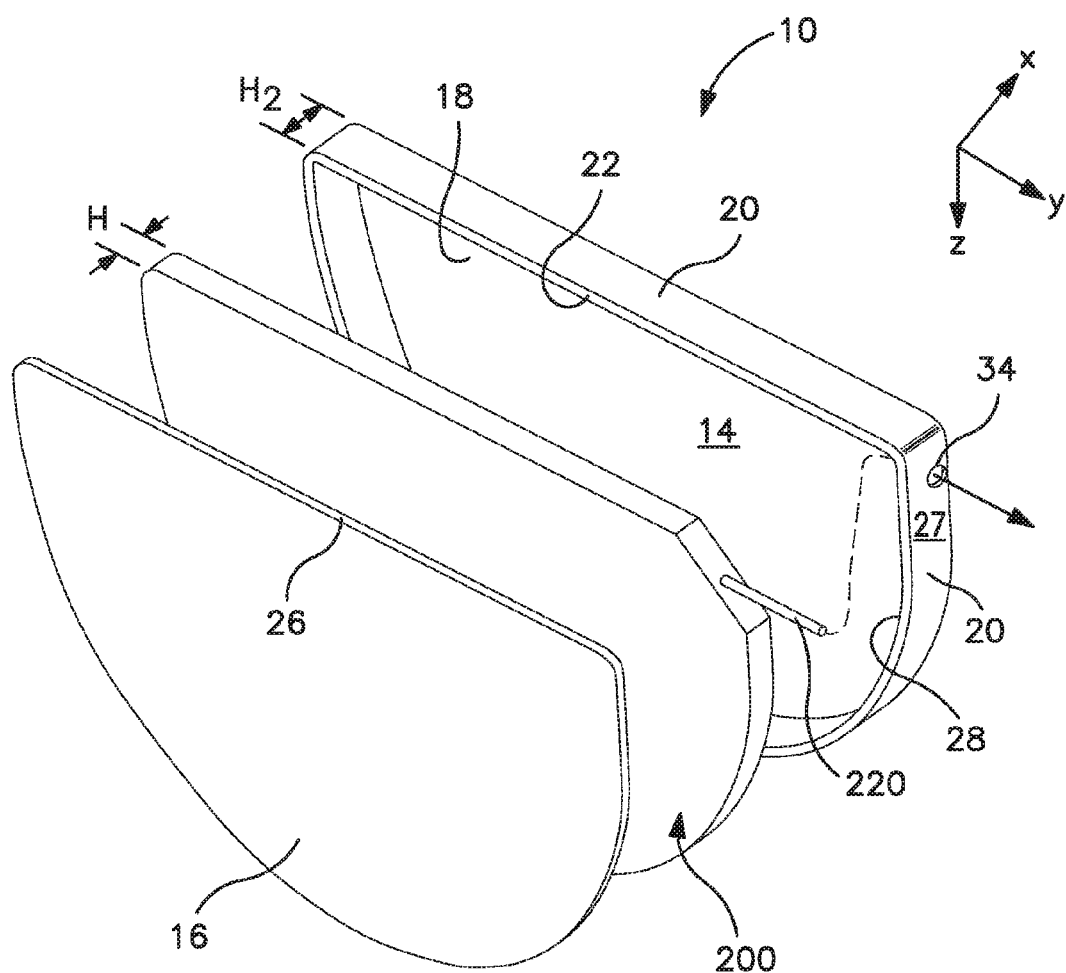
FIG. 4 is a perspective view illustrating the assembly of the anode of FIG. 2 in a casing to form the capacitor shown in FIG. 1.
Figure 5:
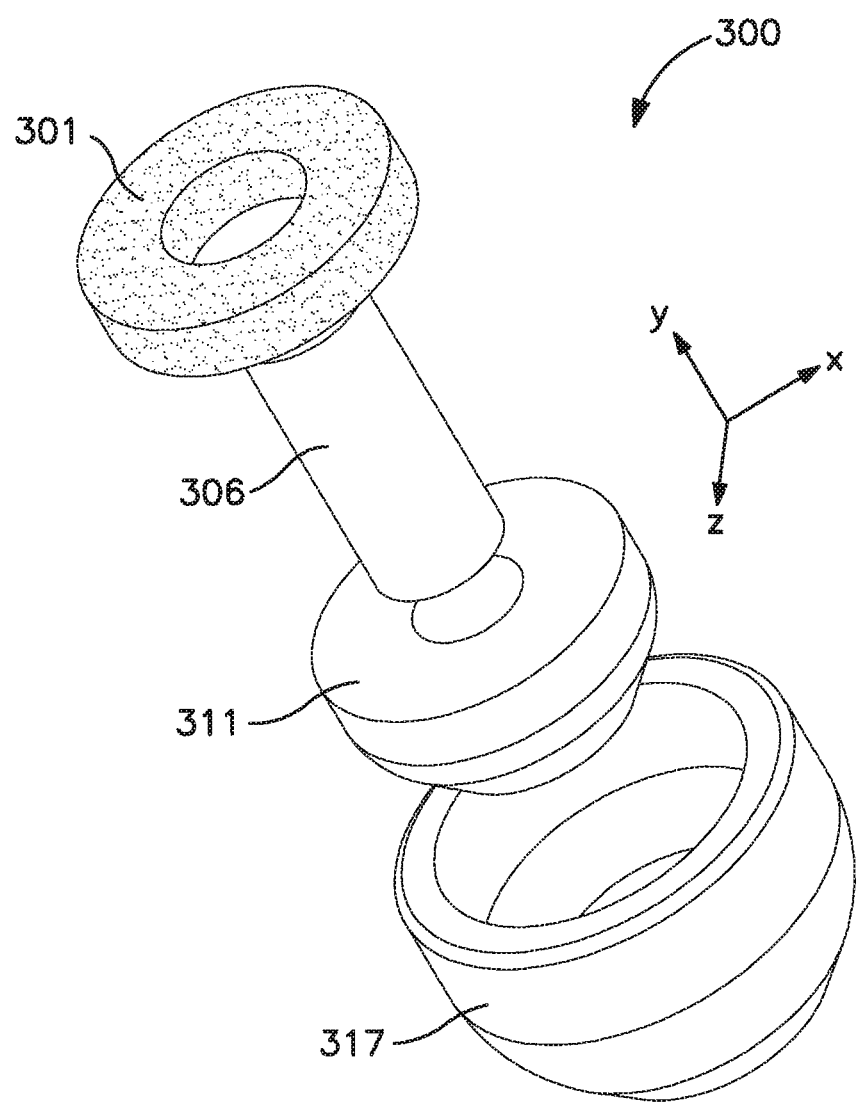
FIG. 5 is an exploded perspective view of the sealing assembly used to hermetically seal the anode lead to the casing at an anode lead orifice in the casing.

Regardless of the particular characteristics of the casing and whether or not it optionally includes the electrochemically-active cathode material of the present invention, the particular manner in which the anode is incorporated into the casing may be accomplished using a variety of techniques. As shown in FIG. 4, the anode 200 may be positioned within the casing 12 made of a first casing member 14 and a second casing member 16. The first casing member 14 can have a face wall 18 joined to a surrounding sidewall 20 having an exterior surface 27 and an interior surface 28 extending to an edge 22. Meanwhile, the second casing member 16 can be in the shape of a plate and can contain a second face wall 24 having a surrounding edge 26. The casing members 14 and 16 may be hermetically sealed together by welding (e.g., laser welding) the overlapping edges 22 and 26 where they contact each other after the anode 200 and sealing assembly 300 have been incorporated into the casing 12 as desired. Regardless of the particular configuration, the casing 12 can have a thickness "$H_2$" of less than about 8 millimeters, such as from about 0.075 millimeters to about 7 millimeters, such as from about 0.1 millimeters to about 6 millimeters, such as from about 0.2 millimeters to about 5 millimeters. Further, the casing members 14 and/or 16 may be analogous to the metal substrate described in reference to the cathode in Section III above such that an electrochemically-active cathode material, such as a conductive polymer coating (not shown), may be deposited on the interior surface thereof. Alternatively, a separate metal substrate may be located adjacent to the casing member 14 and/or 16 and applied with the conductive polymer coating to serve as the cathode. Nevertheless, before welding together the casing members 14 and 16, the anode lead sealing assembly 300 is assembled around the anode lead 220 and sidewall 20 of first casing member 14 to create a hermetic seal at the anode lead orifice 34 as discussed in detail above with reference to Section I.

After assembly of the anode inside the casing and sealing (e.g., welding) as discussed above, the working electrolyte may optionally be introduced into the casing 12 through a fill port 120 as shown in FIG. 1, or by any other suitable means. Filling may be accomplished by placing the capacitor 10 in a vacuum chamber so that the fill port 120 extends into a reservoir of the working electrolyte. When the chamber is evacuated, pressure is reduced inside the capacitor 10. When the vacuum is released, pressure inside the capacitor 10 re-equilibrates, and the electrolyte is drawn through the fill port 120 into the capacitor 10.

In addition to the components discussed above, although not shown, one or more separators may be employed that help insulate the anode and conductive polymer-coated cathode from each other. Examples of suitable materials for this purpose include, for instance, porous polymer materials (e.g., polypropylene, polyethylene, etc.), porous inorganic materials (e.g., fiberglass mats, porous glass paper, etc.), ion exchange resin materials, etc. Particular examples include ionic perfluoronated sulfonic acid polymer membranes (e.g., Nafion™ from the E.I. DuPont de Nemeours & Co.), sulphonated fluorocarbon polymer membranes, polybenzimidazole (PBI) membranes, and polyether ether ketone (PEEK) membranes. Although preventing direct contact between the anode and cathode, the separator permits ionic current flow of the electrolyte to the electrodes.

Regardless of its particular configuration, the capacitor of the present invention may exhibit excellent electrical properties. For example, the capacitor may exhibit a high volumetric efficiency, such as from about 50,000 $\mu F*V/cm^3$ to about 300,000 $\mu F*V/cm^3$, in some embodiments from about 60,000 $\mu F*V/cm^3$ to about 200,000 $\mu F*V/cm^3$, and in some embodiments, from about 80,000 $\mu F*V/cm^3$ to about 150,000 $\mu F*V/cm^3$, determined at a frequency of 120 Hz and at room temperature (e.g., 25° C.). Volumetric efficiency is determined by multiplying the formation voltage of a part by its capacitance, and then dividing by the product by the volume of the part. For example, a formation voltage may be 175 volts for a part having a capacitance of 520 $\mu F$, which results in a product of 91,000 $\mu F*V$. If the part occupies a volume of about 0.8 $cm^3$, this results in a volumetric efficiency of about 113,750 $\mu F*V/cm^3$.

The capacitor may also exhibit a high energy density that enables it suitable for use in high pulse applications. Energy density is generally determined according to the equation $E=\frac{1}{2}*CV^2$, where C is the capacitance in farads (F) and V is the working voltage of capacitor in volts (V). The capacitance may, for instance, be measured using a capacitance meter (e.g., Keithley 3330 Precision LCZ meter with Kelvin Leads, 2 volts bias and 1 volt signal) at operating frequencies of from 10 to 120 Hz (e.g., 120 Hz) and a temperature of 25° C. For example, the capacitor may exhibit an energy density of about 2.0 joules per cubic centimeter ($J/cm^3$) or more, in some embodiments about 3.0 $J/cm^3$, in some embodiments from about 3.5 $J/cm^3$ to about 10.0 $J/cm^3$, and in some embodiments, from about 4.0 to about 8.0 $J/cm^3$. The capacitance may likewise be about 1 milliFarad per square centimeter ("$mF/cm^2$") or more, in some embodiments about 2 $mF/cm^2$ or more, in some embodiments from about 5 to about 50 $mF/cm^2$, and in some embodiments, from about 8 to about 20 $mF/cm^2$. The capacitor may also exhibit a relatively high "breakdown voltage" (voltage at which the capacitor fails), such as about 180 volts or more, in some embodiments about 200 volts or more, and in some embodiments, from about 210 volts to about 260 volts.

The equivalent series resistance ("ESR")—the extent that the capacitor acts like a resistor when charging and discharging in an electronic circuit may also be less than about 15,000 milliohms, in some embodiments less than about 10,000 milliohms, in some embodiments less than about 5,000 milliohms, and in some embodiments, from about 1 to about 4,500 milliohms, measured with a 2-volt bias and 1-volt signal at a frequency of 120 Hz. In addition, the leakage current, which generally refers to the current flowing from one conductor to an adjacent conductor through an insulator, can be maintained at relatively low levels. For example, the numerical value of the normalized leakage current of a capacitor of the present invention is, in some embodiments, less than about 1 $\mu A/\mu F*V$, in some embodiments less than about 0.5 $\mu A/\mu F*V$, and in some embodiments, less than about 0.1 $\mu A/\mu F*V$, where $\mu A$ is microamps and $\mu F*V$ is the product of the capacitance and the rated voltage. Leakage current may be measured using a leakage test meter (e.g., MC 190 Leakage test, Mantracourt Electronics LTD, UK) at a temperature of 25° C. and at a certain rated voltage after a charging time of from about 60 to about 300 seconds. Such ESR and normalized leakage current values may even be maintained after aging for a substantial amount of time at high temperatures. For example, the values may be maintained for about 100 hours or more, in some embodiments from about 300 hours to about 2500 hours, and in some embodiments, from about 400 hours to about 1500 hours (e.g., 500 hours, 600 hours, 700 hours, 800 hours, 900 hours, 1000 hours, 1100 hours, or 1200 hours) at temperatures ranging from about 100° C. to about 250° C., and, in some embodiments from about 100° C. to about 200° C. (e.g., 100° C., 125° C., 150° C., 175° C., or 200° C.).

The electrolytic capacitor of the present invention may be used in various applications, including but not limited to medical devices, such as implantable defibrillators, pacemakers, cardioverters, neural stimulators, drug administering devices, etc.; automotive applications; military applications, such as RADAR systems; consumer electronics, such as radios, televisions, etc.; and so forth. In one embodiment, for example, the capacitor may be employed in an implantable medical device configured to provide a therapeutic high voltage (e.g., between approximately 500 volts and approximately 850 volts, or, desirably, between approximately 600 Volts and approximately 900 volts) treatment for a patient. The device may contain a container or housing that is hermetically sealed and biologically inert. One or more leads are electrically coupled between the device and the patient's heart via a vein. Cardiac electrodes are provided to sense cardiac activity and/or provide a voltage to the heart. At least a portion of the leads (e.g., an end portion of the leads) may be provided adjacent or in contact with one or more of a ventricle and an atrium of the heart. The device may also contain a capacitor bank that typically contains two or more capacitors connected in series and coupled to a battery that is internal or external to the device and supplies energy to the capacitor bank. Due in part to high conductivity, the capacitor of the present invention can achieve excellent electrical properties and thus be suitable for use in the capacitor bank of the implantable medical device.

Regardless of its particular configuration, the capacitor of the present invention may exhibit excellent electrical properties. For example, the capacitor may exhibit a high volumetric efficiency, such as from about 50,000 $\mu F*V/cm^3$ to about 300,000 $\mu F*V/cm^3$, in some embodiments from about 60,000 $\mu F*V/cm^3$ to about 200,000 $\mu F*V/cm^3$, and in some embodiments, from about 80,000 $\mu F*V/cm^3$ to about 150,000 $\mu F*V/cm^3$, determined at a frequency of 120 Hz and at room temperature (e.g., 25° C.). Volumetric efficiency is determined by multiplying the formation voltage of a part by its capacitance, and then dividing by the product by the volume of the part. For example, a formation voltage may be 175 volts for a part having a capacitance of 520 $\mu F$, which results in a product of 91,000 $\mu F*V$. If the part occupies a volume of about 0.8 $cm^3$, this results in a volumetric efficiency of about 113,750 $\mu F*V/cm^3$.

The capacitor may also exhibit a high energy density that enables it suitable for use in high pulse applications. Energy density is generally determined according to the equation $E=\frac{1}{2}*CV^2$, where C is the capacitance in farads (F) and V is the working voltage of capacitor in volts (V). The capacitance may, for instance, be measured using a capacitance meter (e.g., Keithley 3330 Precision LCZ meter with Kelvin Leads, 2 volts bias and 1 volt signal) at operating frequencies of from 10 to 120 Hz (e.g., 120 Hz) and a temperature of 25° C. For example, the capacitor may exhibit an energy density of about 2.0 joules per cubic centimeter ($J/cm^3$) or more, in some embodiments about 3.0 $J/cm^3$, in some embodiments from about 3.5 $J/cm^3$ to about 15.0 $J/cm^3$, and in some embodiments, from about 4.0 to about 12.0 $J/cm^3$. The capacitance may likewise be about 1 milliFarad per square centimeter ("$mF/cm^2$") or more, in some embodiments about 2 $mF/cm^2$ or more, in some embodiments from about 5 to about 50 $mF/cm^2$, and in some embodiments, from about 8 to about 20 $mF/cm^2$. The capacitor may also exhibit a relatively high "breakdown voltage" (voltage at which the capacitor fails), such as about 180 volts or more, in some embodiments about 200 volts or more, and in some embodiments, from about 210 volts to about 260 volts.

The equivalent series resistance ("ESR")—the extent that the capacitor acts like a resistor when charging and discharging in an electronic circuit may also be less than about 15,000 milliohms, in some embodiments less than about 10,000 milliohms, in some embodiments less than about 5,000 milliohms, and in some embodiments, from about 1 to about 4,500 milliohms, measured with a 2-volt bias and 1-volt signal at a frequency of 120 Hz. In addition, the leakage current, which generally refers to the current flowing from one conductor to an adjacent conductor through an insulator, can be maintained at relatively low levels. For example, the numerical value of the normalized leakage current of a capacitor of the present invention is, in some embodiments, less than about 1 $\mu A/\mu F*V$, in some embodiments less than about 0.5 $\mu A/\mu F*V$, and in some embodiments, less than about 0.1 $\mu A/\mu F*V$, where $\mu A$ is microamps and $\mu F*V$ is the product of the capacitance and the rated voltage. Leakage current may be measured using a leakage test meter (e.g., MC 190 Leakage test, Mantracourt Electronics LTD, UK) at a temperature of 25° C. and at a certain rated voltage after a charging time of from about 60 to about 300 seconds. Such ESR and normalized leakage current values may even be maintained after aging for a substantial amount of time at high temperatures. For example, the values may be maintained for about 100 hours or more, in some embodiments from about 300 hours to about 2500 hours, and in some embodiments, from about 400 hours to about 1500 hours (e.g., 500 hours, 600 hours, 700 hours, 800 hours, 900 hours, 1000 hours, 1100 hours, or 1200 hours) at temperatures ranging from about 100° C. to about 250° C., and, in some embodiments from about 100° C. to about 200° C. (e.g., 100° C., 125° C., 150° C., 175° C., or 200° C.).

The electrolytic capacitor of the present invention may be used in various applications, including but not limited to medical devices, such as implantable defibrillators, pacemakers, cardioverters, neural stimulators, drug administering devices, etc.; automotive applications; military applications, such as RADAR systems; consumer electronics, such as radios, televisions, etc.; and so forth. In one embodiment, for example, the capacitor may be employed in an implantable medical device configured to provide a therapeutic high voltage (e.g., between approximately 500 volts and approximately 850 volts, or, desirably, between approximately 600 Volts and approximately 900 volts) treatment for a patient. The device may contain a container or housing that is hermetically sealed and biologically inert. One or more leads are electrically coupled between the device and the patient's heart via a vein. Cardiac electrodes are provided to sense cardiac activity and/or provide a voltage to the heart. At least a portion of the leads (e.g., an end portion of the leads) may be provided adjacent or in contact with one or more of a ventricle and an atrium of the heart. The device may also contain a capacitor bank that typically contains two or more capacitors connected in series and coupled to a battery that is internal or external to the device and supplies energy to the capacitor bank. Due in part to high conductivity, the capacitor of the present invention can achieve excellent electrical properties and thus be suitable for use in the capacitor bank of the implantable medical device.

These and other modifications and variations of the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A wet electrolytic capacitor for an implantable medical device comprising:
 a planar anode that comprises a porous anode body coated with a dielectric layer, wherein an anode lead extends from the porous anode body;
 a working electrolyte that is in electrical contact with the planar anode;
 a casing having an interior within which the planar anode and the working electrolyte are positioned, the casing having a wall that defines an anode lead orifice; and
 a sealing assembly that is connected to the casing at the anode lead orifice, the sealing assembly comprising:
  a metal housing positioned within the anode lead orifice and extending into the interior of the casing, wherein the metal housing defines a cavity through which a portion of the anode lead extends;
  an elastomeric ring positioned within the cavity, wherein the elastomeric ring contains an orifice through which a portion of the anode lead extends; and
  a metal plate positioned within the cavity, wherein the metal plate contains an orifice through which a portion of the anode lead extends, wherein a lower surface of the metal plate is in contact with the elastomeric ring inside the cavity.

2. The wet electrolytic capacitor of claim 1, wherein the sealing assembly further comprises an isolation tube that receives a portion of the anode lead, the isolation tube having a first portion that extends outside the casing and a second portion that extends through the anode lead orifice into the interior of the casing.

3. The wet electrolytic capacitor of claim 2, wherein the isolation tube comprises an insulative material.

4. The wet electrolytic capacitor of claim 1, wherein the elastomeric ring and the cavity of the metal housing each have a tapered portion, wherein the tapered portion of the elastomeric ring is located inside the cavity at the tapered portion of the cavity.

5. The wet electrolytic capacitor of claim 1, wherein the metal housing comprises titanium or an alloy thereof.

6. The wet electrolytic capacitor of claim 1, wherein the metal plate comprises titanium or an alloy thereof.

7. The wet electrolytic capacitor of claim 1, wherein an electrochemically active cathode material is disposed on at least a portion of the casing.

8. The wet electrolytic capacitor of claim 7, wherein the electrochemically active cathode material includes a conductive polymer.

9. The wet electrolytic capacitor of claim 8, wherein the conductive polymer is poly(3,4-ethylenedioxythiophene).

10. The wet electrolytic capacitor of claim 1, wherein the casing contains titanium or an alloy thereof.

11. The wet electrolytic capacitor of claim 1, wherein the porous anode body includes tantalum, niobium, or an electrically conductive oxide thereof.

12. The wet electrolytic capacitor of claim 1, wherein the anode lead comprises tantalum.

13. The wet electrolytic capacitor of claim 1, further comprising a separator that surrounds at least a portion of the planar anode.

14. The wet electrolytic capacitor of claim 1, wherein the sealing assembly provides a hermetic seal at the anode lead orifice.

15. An implantable cardioverter defibrillator comprising the wet electrolytic capacitor of claim 1.

16. A method for forming a wet electrolytic capacitor for use in an implantable medical device, the method comprising:
 positioning a planar porous anode body having an anode lead extending therefrom inside a casing having a sidewall in which an anode lead orifice is formed such that a portion of the anode lead extends through the anode lead orifice, wherein a sealing assembly surrounds the anode lead at the anode lead orifice, the sealing assembly comprising a metal housing positioned within the anode lead orifice and extending into an interior of the casing, wherein the metal housing defines a cavity through which a portion of the anode lead extends; an elastomeric ring positioned within the cavity, wherein the elastomeric ring contains an orifice through which a portion of the anode lead extends; and a metal plate positioned within the cavity, wherein the metal plate contains an orifice through which a portion of the anode lead extends, wherein a lower surface of the metal plate is in contact with the elastomeric ring inside the cavity; and
 forming a hermetic seal between the sealing assembly and the anode lead.

17. The method of claim 16, wherein the metal plate and the elastomeric ring are welded together to create the hermetic seal.

18. The method of claim 16, further comprising welding the metal housing to the casing.

19. The method of claim 16, wherein the sealing assembly further comprises an isolation tube that receives a portion of the anode lead, the isolation tube having a first portion that extends outside the casing and a second portion that extends through the anode lead orifice into the interior of the casing.

20. The method of claim 19, wherein the isolation tube comprises an insulative material.

21. The method of claim 16, wherein the metal housing comprises titanium or an alloy thereof.

22. The method of claim 16, wherein the metal plate comprises titanium or an alloy thereof.

23. The method of claim 16, wherein at least a portion of the casing is coated with an electrochemically-active cathode material.

24. The method of claim 16, further comprising introducing a working electrolyte inside the casing.

* * * * *